(12) United States Patent
Nishiyama et al.

(10) Patent No.: US 11,890,347 B2
(45) Date of Patent: Feb. 6, 2024

(54) PH-RESPONSIVE POLYMER AND DRUG DELIVERY SYSTEM

(71) Applicant: Tokyo Institute of Technology, Tokyo (JP)

(72) Inventors: Nobuhiro Nishiyama, Tokyo (JP); Hiroyasu Takemoto, Tokyo (JP); Abdul-Hackam Ranneh, Tokyo (JP); Keishiro Tomoda, Tokyo (JP); Takahiro Nomoto, Tokyo (JP); Makoto Matsui, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 4 days.

(21) Appl. No.: 16/468,199

(22) PCT Filed: Dec. 5, 2017

(86) PCT No.: PCT/JP2017/043604
§ 371 (c)(1),
(2) Date: Jun. 10, 2019

(87) PCT Pub. No.: WO2018/110366
PCT Pub. Date: Jun. 21, 2018

(65) Prior Publication Data
US 2020/0069807 A1    Mar. 5, 2020

(30) Foreign Application Priority Data

Dec. 15, 2016   (JP) ................. 2016-243749

(51) Int. Cl.
*A61K 47/59* (2017.01)
*C08G 69/48* (2006.01)

(52) U.S. Cl.
CPC .............. *A61K 47/59* (2017.08); *C08G 69/48* (2013.01)

(58) Field of Classification Search
None
See application file for complete search history.

(56) References Cited

U.S. PATENT DOCUMENTS

2012/0053295 A1   3/2012  Kataoka et al.

FOREIGN PATENT DOCUMENTS

| JP | 2000086757 A | 3/2000 |
| JP | 2003 286344 * | 10/2003 |
| JP | 2003286344 | 10/2003 |
| JP | 2011231220 A | 11/2011 |
| WO | WO-2010093036 A1 | 8/2010 |

OTHER PUBLICATIONS

Maeda et al. (Macromol. Rapid Commun., 35, 1211-1215, 2014) Fine-Tuning of Charge-Conversion Polymer . . . .*
Deming et al. (Chem. Rev. 2016, 116, 786-808 which is published online on Jul. 6, 2015) Synthesis of Side-Chain Modified Polypeptides.*
Zhang et al. (Bioconjugate Chem. 2009, 20, 440-446) Polyaspartamide-Based Oligo-ethylenimine Brushes with High Buffer Capacity and Low Cytotoxicity for Highly Efficient Gene Delivery.*
"European Application No. 17881482.8 Office Action dated Jul. 24, 2020", 7 pgs.
"International Application Serial No. PCT/JP2017/043604, International Search Report dated Feb. 27, 2018", w/ English Translation, (Feb. 27, 2018), 4 pgs.
"International Application Serial No. PCT/JP2017/043604, Written Opinion dated Feb. 27, 2018", (Feb. 27, 2018), 3 pgs.
Iwasaki, Takashi, et al., "Cellular uptake and in vivo distribution of polyhistidine peptides", Journal of Controlled Release, vol. 210, (Jul. 28, 2015), 115-124.
Knop, K., et al., "Poly(ethylene glycol) in drug delivery: pros and cons as well as potential alternatives", Angew. Chem. Int. Ed., 49, (2010), 6288-6308.
Tangsangasaksri, Montira, et al., "siRNA-Loaded Polyion Complex Micelle Decorated with Charge-Conversional Polymer Tuned to Undergo Stepwise Response to Intra-Tumoral and Intra-Endosomal", pHs for Exerting Enhanced RNAi Efficacy, Biomacromolecules, vol. 17, No. 1, (Nov. 30, 2015), 246-255.
"Japanese Application Serial No. 2018-556597, Office Action dated Sep. 14, 2021", w/ English Translation, (Sep. 14, 2021), 7 pgs.
Liu, Shuai, et al., "Polycation-based ternary gene delivery system", Current drug metabolism 16.2, (2015), 152-165.
Miyata, Kanjiro, et al., "Polymeric micelles for nano-scale drug delivery", Reactive and Functional Polymers 71.3, (Nov. 2, 2010), 227-234.
Suma, Tomoya, et al., "Enhanced stability and gene silencing ability of siRNA-loaded polyion complexes formulated from polyaspartamide derivatives with a repetitive array of amino groups in the side chain", Biomaterials 33.9, (Dec. 24, 2011), 2770-2779.
Zhou, Zhuxian, et al., "Linear polyethyleneimine-based charge-reversal nanoparticles for nuclear-targeted drug delivery", Journal of Materials Chemistry 21.47, (Oct. 26, 2011), 19114-19123.

* cited by examiner

Primary Examiner — Tigabu Kassa
(74) Attorney, Agent, or Firm — Schwegman Lundberg & Woessner, P.A.

(57) ABSTRACT

A pH-responsive polymer formed of a biocompatible polymer to which a group which is electrically neutral under pH environments of more than 7 and which changes to be cationic at pH 7 or less is bonded.

9 Claims, 6 Drawing Sheets

PH-RESPONSIVE POLYMER AND DRUG DELIVERY SYSTEM

PRIORITY APPLICATIONS

This application is a U.S. National Stage Filing under 35 U.S.C. 371 from International Application No. PCT/JP2017/043604, filed on Dec. 5, 2017, and published as WO2018/110366 on Jun. 21, 2018, which claims the benefit of priority to Japanese Application No. 2016-243749, filed on Dec. 15, 2016; the benefit of priority of each of which is hereby claimed herein, and which applications and publication are hereby incorporated herein by reference in their entirety.

TECHNICAL FIELD

The present invention relates to a pH-responsive polymer and a drug delivery system. This application claims priority based on Japanese Patent Application No. 2016-243749 filed in Japan on Dec. 15, 2016, the content of which is hereby incorporated by reference.

BACKGROUND ART

In the related art, polymers are used to control the in vivo dynamics of drugs and the like. These polymers enable long-term blood retention of drugs or the like by exhibiting a stealth property which suppresses random interaction between drugs and the like and normal tissue and blood components, and enable the suppression of toxicity in normal tissue and, at the same time, the accumulation in tumor tissue. As such polymers, for example, polyethylene glycol (PEG) and the like have been used (refer to for example, NPL 1).

CITATION LIST

Patent Literature

Non-Patent Literature

[NPL 1] Knop K., et al., Poly(ethylene glycol) in drug delivery: pros and cons as well as potential alterations. Angew. Chem. Int. Ed., 49, 6288-6208, 2010

SUMMARY OF INVENTION

Technical Problem

However, the related art polymers exhibiting a stealth property in vivo may suppress not only the interaction with blood components and normal tissue, but also the interaction with tumor tissue. As a result, the accumulation of drugs or the like in tumor tissue as a target site and the incorporation of drugs or the like into cancer cells may not be efficient.

In view of the above, it is an object of the present invention to provide a polymer exhibiting a stealth property with respect to blood components and normal tissue, and with improved accumulation efficiency and incorporation efficiency into cells with respect to tumor tissue.

Solution to Problem

The present invention includes the following aspects.

[1] A pH-responsive polymer including a biocompatible polymer to which a group which is electrically neutral under pH environments of more than 7 and which changes to be cationic at pH 7 or less is bonded.

[2] The pH-responsive polymer according to [1], in which the group which is electrically neutral under pH environments of more than 7 and which changes to be cationic at pH 7 or less is a group which is electrically neutral under pH environments of 7.2 to 7.6 and which changes to be cationic under pH environments of 6.0 to 6.6.

[3] The pH-responsive polymer according to [1] or [2], in which the group which is electrically neutral under pH environments of more than 7 and which changes to be cationic at pH 7 or less includes a group represented by Formula (a)

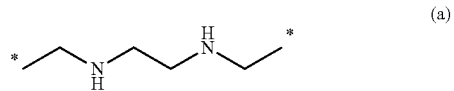

[in Formula (a), * represents a bond].

[4] The pH-responsive polymer according to any one of [1] to [3], in which the group which is electrically neutral under pH environments of more than 7 and which changes to be cationic at pH 7 or less includes a carboxyl group, a sulfo group, or a phosphonic group.

[5] The pH-responsive polymer according to [4], in which the group including the carboxyl group is a group represented by Formula (1), the group including the sulfo group is a group represented by Formula (2), and the group including the phosphonic group is a group represented by Formula (3)

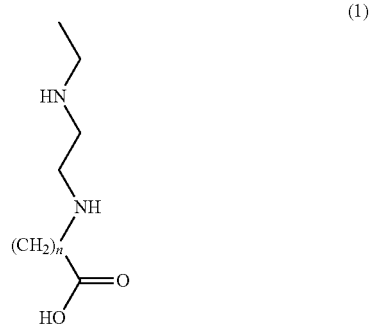

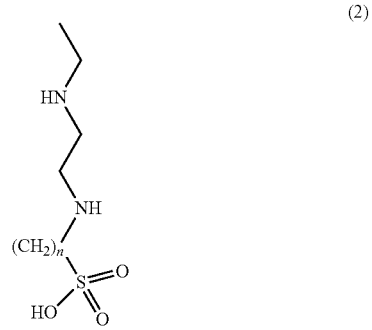

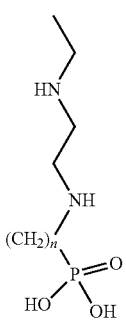

(3)

[in Formulas (1) to (3), n represents an integer of 1 to 3, and * represents a bond].

[6] The pH-responsive polymer according to any one of [1] to [5], in which the biocompatible polymer is biodegradable.

[7] The pH-responsive polymer according to [6], in which the biocompatible polymer is selected from the group consisting of polyamino acids, polyesters, polynucleotides, and polysaccharides.

[8] The pH-responsive polymer according to [7], in which the biocompatible polymer is a polyamino acid.

[9] The pH-responsive polymer according to [8], in which the polyamino acid is polyglutamic acid or polyaspartic acid.

[10] The pH-responsive polymer according to [9], including a repeating unit represented by Formula (b).

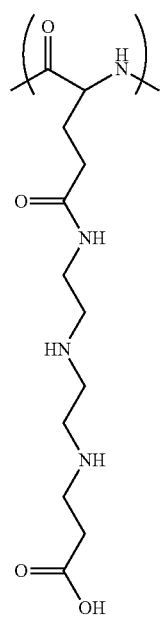

(b)

[11] The pH-responsive polymer according to [9], including a repeating unit represented by Formula (c)

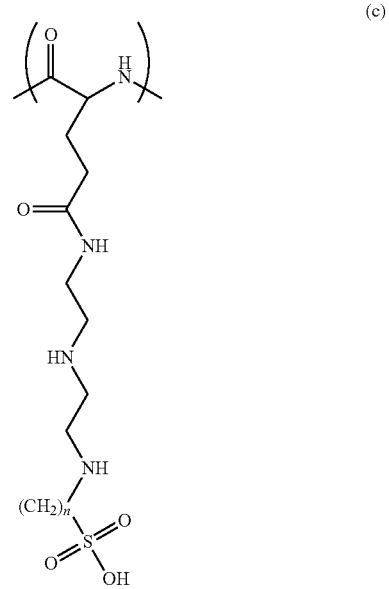

(c)

[in Formula (c), n represents 2 or 3].

[12] The pH-responsive polymer according to any one of [1] to [11], in which a weight-average molecular weight is 1,000 to 200,000.

[13] The pH-responsive polymer according to [12], in which a weight-average molecular weight is 10,000 to 50,000.

[14] The pH-responsive polymer according to any one of [1] to [13], in which 4 to 800 mol of the group which is electrically neutral under pH environments of more than 7 and which changes to be cationic at pH 7 or less is bonded per one mol of the biocompatible polymer.

[15] The pH-responsive polymer according to any one of [1] to [14], which is for a drug delivery system.

[16] A drug delivery system in which a drug and the pH-responsive polymer according to any one of [1] to [15] are bonded to each other.

Advantageous Effects of Invention

According to the present invention, it is possible to provide a polymer exhibiting a stealth property with respect to blood components and normal tissue, and with improved accumulation efficiency and incorporation efficiency into cells with respect to tumor tissue.

BRIEF DESCRIPTION OF DRAWINGS

FIG. 3(a) is a test result at pH 7.4, FIG. 3(b) is a test result at pH 6.5, and FIG. 3(c) is a test result at pH 5.5.

FIG. 4(a) shows the result at pH 7.4 and FIG. 4(b) shows the result at pH 6.7.

DESCRIPTION OF EMBODIMENTS

[pH-Responsive Polymer]

Figure 1:
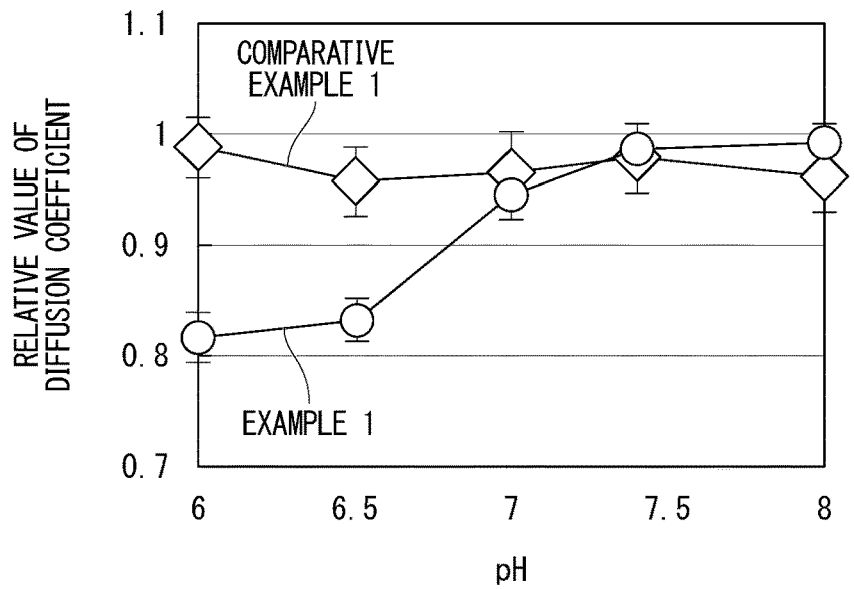
FIG. 1 is a graph showing results of measuring the diffusion coefficient of a polymer by fluorescence correlation spectroscopy in Experimental Example 1.

In one embodiment, the present invention provides a pH-responsive polymer including a biocompatible polymer to which a group which is electrically neutral under pH environments of more than 7 and which changes to be cationic at pH 7 or less is bonded.

Blood components and the peripheral normal tissue in living bodies are kept almost neutral at pH 7.4. In contrast, the peripheral environment of tumor tissue is a weakly acidic pH condition (approximately pH 6.5 or lower). As described below in the Examples, the pH-responsive polymer of the present embodiment is electrically neutral under pH environments of more than 7, for example, under pH environments (pH 7.4) corresponding to normal tissue, and exhibits a stealth property with respect to blood components and normal tissue. On the other hand, the pH-responsive polymer is cationic at a pH of 7 or less, for example, at approximately pH 6.5 or lower corresponding to a weakly acidic environment in the periphery of the tumor tissue. For this reason, the pH-responsive polymer of the present embodiment does not induce interaction with anionic molecules such as heparin present on the cell surface in normal tissue, but does induce interaction in cancer tissue, thereby being efficiently incorporated into cancer cells.

Accordingly, using the pH-responsive polymer of the present embodiment makes it possible to efficiently deliver a drug to tumor tissue and to suppress damage to normal tissue. Therefore, the pH-responsive polymer of the present embodiment is particularly useful for constructing a drug delivery system for treating cancer. That is, it may be said that the pH-responsive polymer of the present embodiment is for a drug delivery system.

In the pH-responsive polymer of the present embodiment, the group which is electrically neutral under pH environments of more than 7 and which changes to be cationic at pH 7 or less is preferably a group which is electrically neutral under pH environments of 7.2 to 7.6 and which changes to be cationic under pH environments of 6.0 to 6.6.

In the pH-responsive polymer of the present embodiment, the biocompatible polymer means a polymer which, in a case of being administered to a living body, is less likely to have an adverse influence such as a strong inflammatory reaction. The biocompatible polymer is not particularly limited as long as it is possible to obtain the effect of the present invention, and examples thereof include polyamino acid, polyacrylamide, polyether, polyester, polyurethane, polynucleotide, polysaccharide, and the like, and polyamino acid, polyacrylamide, and polysaccharides are preferable.

The biocompatible polymer may have an arbitrary group introduced into a part thereof in the synthetic process thereof. Examples of such a group include a part of a polymerization initiator and the like. The biocompatible polymer is preferably neutral or near neutral in the charge balance within the polymer molecule.

In the pH-responsive polymer of the present embodiment, the biocompatible polymer is preferably biodegradable. In the present specification, that the biocompatible polymer is biodegradable means that at least a part of the biocompatible polymer is biodegradable. In a case where the polymers of the related art are administered to a living body, the accumulation thereof in the living body may be a problem. On the other hand, using a biodegradable polymer makes it possible to suppress accumulation in the living body, and to reduce side effects.

Biodegradable means a property of being absorbable or decomposable in vivo. The biocompatible polymer which is biodegradable is not particularly limited as long as it is possible to obtain the effect of the present invention, and examples thereof include polyamino acids, polyesters, polynucleotides, polysaccharides, and the like, and polyamino acids and polysaccharides are preferable, and a polyamino acid is more preferable. As the polyamino acid, polyglutamic acid or polyaspartic acid is preferable.

The pH-responsive polymer of the present embodiment is able to exhibit pH-responsiveness due to the group which is electrically neutral under pH environments of more than 7 and which changes to be cationic at pH 7 or less being bonded. The pH-responsiveness is a property in which an electric charge changes in response to the peripheral pH environment. As will be described below in the Examples, the pH-responsive polymer of the present embodiment is able to exhibit a greater stealth property compared with the PEG used in the related art.

In the pH-responsive polymer of the present embodiment, the group which is electrically neutral under pH environments of more than 7 and which changes to be cationic at pH 7 or less preferably includes a group represented by Formula (a) as a part of the group.

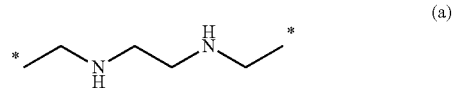

(a)

[in Formula (a), * represents a bond.]

It is also possible for the group represented by Formula (a) to be a group having an ethylenediamine structure. As described below, a group having an ethylenediamine structure is able to exhibit a change in the number of electric charges according to changes in the pH environment.

In the pH-responsive polymer of the present embodiment, the group which is electrically neutral under pH environments of more than 7 and which changes to be cationic at pH 7 or less preferably includes, for example, an anionic group such as a carboxyl group represented by Formula (4), a sulfo group represented by Formula (5), and a phosphonic group represented by Formula (6) as a part of the group.

(4)

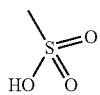

(5)

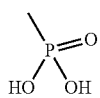

(6)

In the pH-responsive polymer of the present embodiment, the group which is electrically neutral under pH environments of more than 7 and which changes to be cationic at pH 7 or less preferably has a structure represented by Formula (1), (2), or (3).

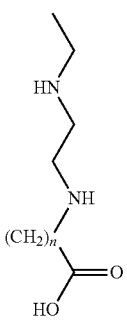

(1)

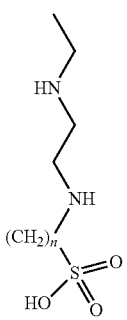

(2)

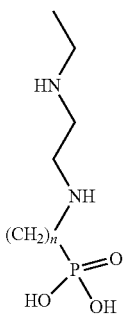

(3)

[in the Formulas (1) to (3), n represents an integer of 1 to 3, and * represents a bond.]

The group represented by Formula (1) is a specific example of a group including a carboxyl group represented by Formula (4). In addition, the group represented by Formula (2) is a specific example of a group including a sulfo group represented by Formula (5). In addition, the group represented by Formula (3) is a specific example of a group including a phosphonic group represented by Formula (6).

Here, a description will be given of a change in the number of charges according to the pH environment by taking a group in which n is 2 in the group represented by Formula (1) as an example. Formula (7) shows a group in which n is 2 in the group represented by Formula (1). The group shown by Formula (7) has an ethylenediamine structure and a carboxyl group which is an anionic group.

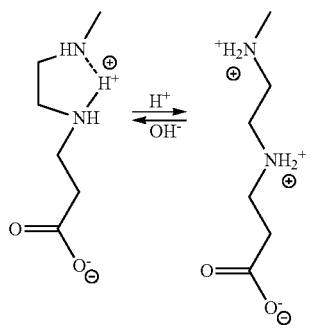

(7)

The ethylenediamine structure has two pKa (6.2 and 8.9). As shown on the left side of Formula (7), under pH environments (pH 7.4) corresponding to normal tissue, the number of cationic charges of the ethylenediamine structure is 1.

However, when the pH decreases, the number of cationic charges of the ethylenediamine structure changes to 2 as shown on the right side of Formula (7).

For this reason, the group having the ethylenediamine structure and the anionic group balances electric charges in the pH environment (pH 7.4) corresponding to the normal tissue to become electrically neutral, and is able to exhibit a stealth property. In addition, when the pH is approximately 6.5 or less corresponding to the weakly acidic peripheral environment of the tumor tissue, the group becomes cationic.

As a result, the biocompatible polymer in which the group having the ethylenediamine structure and the anionic group are bonded is able to exhibit a stealth property with respect to blood components and normal tissue, and is able to exhibit high accumulation efficiency and high incorporation efficiency into cells with respect to tumor tissue.

As will be described below in the Examples, the pH-responsive polymer having a group represented by Formulas (1), (2), or (3) is able to exhibit a stealth property with respect to blood components and normal tissue, and is able to exhibit high accumulation efficiency and high incorporation efficiency into cells with respect to tumor tissue.

The pH-responsive polymer of the present embodiment preferably has a weight-average molecular weight of 1,000 to 200,000 and the weight-average molecular weight may be, for example, 5,000 to 100,000, or, for example, 10,000 to 50,000.

Here, as the weight-average molecular weight of the pH-responsive polymer, it is possible to use a value measured by size-exclusion chromatography (SEC) analysis. Specifically, after dissolving the pH-responsive polymer in a solvent, the result is passed through a column using a filler in which many pores are present together with a mobile phase solution, separated depending on the size of the molecular weight in the column, and subjected to detection using a differential refractometer, an ultraviolet-visible spectrophotometer, a viscometer, a light-scattering detector, or the like as detectors. SEC apparatuses are widely available and it is common to carry out measurement using a standard polyethylene glycol equivalent. In the present specification, the weight-average molecular weight is measured in terms of this standard polyethylene glycol conversion.

In the pH-responsive polymer of the present embodiment, the group which is electrically neutral under pH environments of more than 7 and which changes to be cationic at pH 7 or less is preferably bonded at 4 to 800 mol per mol of the above-described biocompatible polymer, and may be, for example, 20 to 400 mol, for example, 40 to 200 mol, or, for example, 60 to 130 mol.

In a case where the biocompatible polymer is a polyamino acid, preferable specific examples of the pH-responsive polymer of the present embodiment include a polymer in which any one of Formulas (1) to (3) is bonded to a side chain of poly-L-glutamic acid or poly-L-aspartic acid, preferably a polymer represented by Formula (A1).

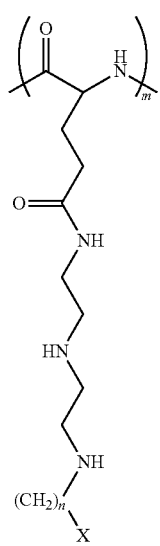

(A1)

[in Formula (A1), m represents an integer of 4 to 800, n represents an integer of 1 to 3, and X represents a group represented by Formula (4) or Formula (5).]

The pH-responsive polymer of the present embodiment may include a repeating unit represented by Formula (b), or may include a repeating unit represented by Formula (c).

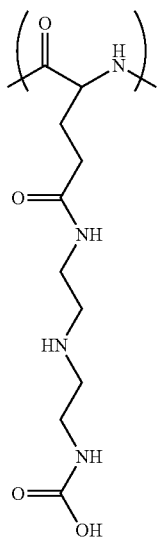

(b)

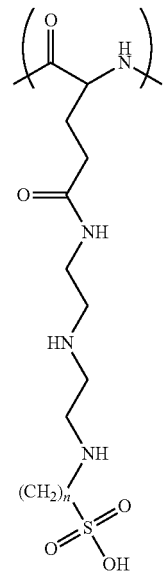

(c)

[in Formula (c), n represents 2 or 3.]

In addition, in a case where the biocompatible polymer is polyacrylamide, a preferable specific example of the pH-responsive polymer of the present embodiment is a polymer represented by Formula (A2).

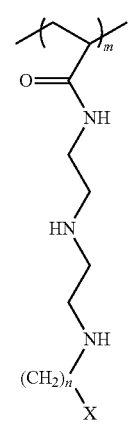

(A2)

[in Formula (A2), m represents an integer of 4 to 800, n represents an integer of 1 to 3, and X represents a group represented by Formula (4) or Formula (5).]

Furthermore, in a case where the biocompatible polymer is a polysaccharide, preferable specific examples of the pH-responsive polymer of the present embodiment include a polymer in which any one of Formulas (1) to (3) is bonded to the side chain of carboxymethylcellulose, hyaluronic acid, pullulan, chitosan, dextran, and cyclodextrin, and a polymer represented by Formula (A3) is preferable.

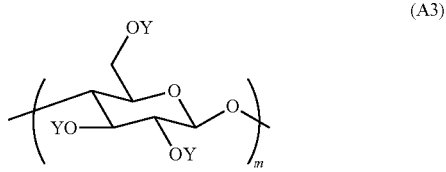

(A3)

[in the Formula (A3), m represents 4 to 500, each Y independently represents a group represented by Formula (A4) or a hydrogen group, at least one of which is a group represented by Formula (A4).]

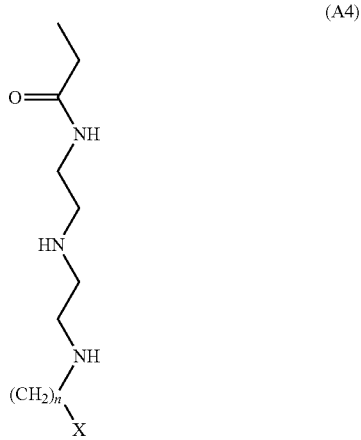

(A4)

[in the Formula (A4), n represents an integer of 1 to 3, X represents a group represented by Formula (4) or Formula (5), and * represents a bond.]

Next, a description will be given of preferable specific examples of the method for producing a pH-responsive polymer. For example, it is possible to obtain the pH-responsive polymer of the present invention by introducing a diethylene triamine into a biocompatible polymer having a carboxyl group or a carboxyl group protected with a protective group (for example, a benzyl group, a methyl group, an ethyl group, or the like) in a side chain by a condensation reaction using a known condensing agent or the like or an aminolysis reaction to synthesize an amine polymer, and introducing a group including the group represented by Formula (4) or Formula (5) by carrying out a Michael addition reaction or a nucleophilic substitution reaction with respect to the obtained amine polymer.

In addition, in a case of a biocompatible polymer not having a carboxyl group or a carboxyl group protected with a protective group in the side chain, it is possible to obtain the pH-responsive polymer of the present embodiment by introducing a carboxyl group or the like into the side chain by a known method using chloroacetic acid, succinic anhydride, chloroformic acid-p-nitrophenyl, or the like, synthesizing an amine polymer by the same condensation reaction or aminolysis reaction as described above, and carrying out a Michael addition reaction or a nucleophilic substitution reaction with respect to the obtained amine polymer.

In a case where the biocompatible polymer is a polyamino acid, it is possible to produce the biocompatible polymer which has a carboxyl group or a carboxyl group protected with a protective group in the side chain with a known production method such as ring-opening polymerization of amino acid-N-carboxyanhydride such as β-benzyl-L-glutamic acid-N-carboxyanhydride (BLG-NCA), in which an amine compound is an initiator. Alternatively, commercially available polyamino acids may be used.

In addition, in a case where the biocompatible polymer is polyacrylamide, it is possible to produce a biocompatible polymer having a carboxyl group or a carboxyl group protected with a protective group in the side chain using a known production method such as free radical polymerization or living radical polymerization in which acrylic acid or benzyl acrylate is used as a raw material.

Furthermore, in a case where the biocompatible polymer is a polysaccharide, it is possible to use commercially available carboxymethyl cellulose, hyaluronic acid, or the like as the biocompatible polymer having a carboxyl group in the side chain.

(Description of Method of Introducing Group Having Ethylenediamine Structure into Biocompatible Polymer)

In a case of a biocompatible polymer having a carboxyl group protected by a protective group in the side chain, it is possible to obtain a biocompatible polymer (amine polymer) into which a group having an ethylenediamine structure is introduced by the reaction of the polymer with diethylenetriamine or by introducing diethylenetriamine using a known condensing agent or the like with respect to a carboxylic acid obtained by deprotecting the polymer.

It is possible to perform this reaction in various solvents. The solvent is not particularly limited as long as the solvent is not reactive with the polymer and diethylenetriamine, and examples thereof include various organic solvents such as tetrahydrofuran, acetonitrile, chloroform, DMF and NMP, and mixtures thereof. From the viewpoint of solubility of the polymer, NMP or tetrahydrofuran is preferable. The amount of the solvent to be used is generally 1 to 100 times the mass ratio with respect to the polymer, preferably 3 to 50 times, and most preferably 5 to 30 times.

The use amount of diethylenetriamine in this reaction is generally 30 to 150 times in terms of molar ratio with respect to the carboxyl group protected with the protective group of the polymer, preferably 40 to 100 times, and more preferably 50 to 80 times. In a case where the use amount of diethylenetriamine is less than 30 times, there is a concern that a structure in which the polymers are cross-linked by diethylenetriamine may be formed, and in a case of more than 150 times, it may be difficult to remove unreacted diethylenetriamine.

In addition, it is possible to use a catalyst for this reaction, and for example, it is possible to use a catalyst such as 2-hydroxypyridine, pyridine, triethylamine, or the like.

The reaction temperature in a case of carrying out this reaction varies depending on the solvent to be used, but is generally from 0 to 100° C. In addition, the reaction time varies depending on the conditions of the reaction temperature, but is generally preferably approximately 1 to 48 hours. It is also possible to use the amine polymer obtained by this reaction as it is without purification, or it is also possible to perform isolation and purification by a treatment such as column chromatography.

On the other hand, in a case of a biocompatible polymer having a carboxyl group in the side chain, it is possible to obtain an amine polymer by carrying out a condensation reaction on the polymer with diethylenetriamine in the presence of a condensing agent. In addition, in a case of a biocompatible polymer having a carboxyl group protected by a protective group on the side chain, it is possible to obtain an amine polymer by removing the protection of the protective group by a known reaction to obtain a biocompatible polymer having a carboxyl group in the side chain and then carrying out a condensation reaction in the same manner.

It is possible to carry out this reaction in various solvents, and the solvent to be used is not particularly limited as long as the solvent is not reactive with the polymer, diethylenetriamine, and condensing agent, and examples thereof include various organic solvents such as tetrahydrofuran, acetonitrile, chloroform, DMF, and NMP, and mixtures thereof. From the viewpoint of solubility of the polymer, NMP or tetrahydrofuran is preferable. The use amount of the solvent is generally 1 to 100 times the weight ratio with respect to the biocompatible polymer, preferably 3 to 50 times, and more preferably 5 to 30 times.

The use amount of diethylenetriamine in this reaction is generally 30 to 150 times with respect to the carboxyl group of the polymer, preferably 40 to 100 times, and more preferably 50 to 80 times, in terms of molar ratio. In a case where the use amount of diethylenetriamine is less than 30 times, there is a concern that a structure in which the polymers are cross-linked by diethylenetriamine may be formed, and in a case of being more than 150 times, it may be difficult to remove unreacted diethylenetriamine.

The condensing agent used in this reaction is not particularly limited as long as the reaction proceeds and, for example, it is possible to use N,N'-dicyclohexylcarbodiimide, 1-(3-dimethylaminopropyl)-3-ethylcarbodiimide hydrochloride, and the like.

The reaction temperature in a case of carrying out this reaction varies depending on the solvent to be used, but is generally from 10 to 100° C. In addition, the reaction time varies depending on the conditions such as the reaction temperature, but is generally preferably approximately 1 to 48 hours. The amine polymer obtained by this reaction is preferably isolated and purified by removing the condensing agent by a treatment such as crystallization or column chromatography.

(Description of Method of Introducing Group Including Formula (4) or Formula (5) into Amine Polymer)

It is possible to introduce the group including Formula (4) or Formula (5) into the amine polymer by a Michael addition reaction or a nucleophilic substitution reaction.

In the case of a Michael addition reaction, it is possible to obtain the pH-responsive polymer by performing the Michael addition reaction between the amine polymer and acrylic acid, vinylsulfonic acid, or a sodium salt or a potassium salt thereof in an aqueous solution having a pH of 9 to 10.

The use amount of acrylic acid, vinylsulfonic acid, or the sodium salt or potassium salt thereof used in the Michael addition reaction is generally 3 to 300 times in terms of molar ratio with respect to the primary amino group of the side chain of the amine polymer.

The Michael addition reaction is carried out in an aqueous solution of pH 9 to 10. For adjustment of the pH, an inorganic base is generally used. Specifically, it is possible to use sodium hydroxide, sodium carbonate, potassium hydroxide, potassium carbonate, or the like.

The reaction temperature in a case where the Michael addition reaction is carried out is generally 0 to 80° C. In addition, the reaction time varies depending on conditions such as the reaction temperature, but is generally preferably approximately 5 hours to 2 weeks.

The pH-responsive polymer obtained by this reaction may be used as it is without purification, or may be isolated and purified by a treatment such as column chromatography.

In a case of a nucleophilic substitution reaction, it is possible to obtain the pH-responsive polymer of the present embodiment by subjecting the amine polymer to a nucleophilic substitution reaction with 4-bromobutanoic acid or sodium 3-bromopropanesulfonate.

The use amount of 4-bromobutanoic acid or sodium 3-bromopropanesulfonate used in the nucleophilic substitution reaction is generally 3 to 300 times in terms of molar ratio with respect to the primary amino group of the side chain of the amine polymer.

In the nucleophilic substitution reaction, a basic catalyst may be used, and for example, it is possible to use inorganic bases such as sodium hydroxide, sodium carbonate, potassium hydroxide, or potassium carbonate.

The reaction temperature in a case of performing a nucleophilic substitution reaction is generally 0 to 80° C. In addition, the reaction time varies depending on the conditions such as the reaction temperature, but is generally preferably approximately 5 hours to 1 week.

The pH-responsive polymer obtained by this reaction may be used as it is without purification, or may be isolated and purified by a treatment such as column chromatography.

[Drug Delivery System]

In one embodiment, the present invention provides a drug delivery system in which a drug and the above-described pH-responsive polymer are bonded to each other.

As will be described below in the Examples, the drug delivery system of the present embodiment exhibits a stealth property with respect to blood components and normal tissue, and exhibits high accumulation efficiency and incorporation efficiency into cells with respect to tumor tissue. Accordingly, using the drug delivery system of the present embodiment makes it possible to efficiently deliver the drug to the tumor tissue and to suppress damage to the normal tissue.

In the drug delivery system of the present embodiment, the drug is not particularly limited, and examples thereof include an inhibitory nucleic acid, a low-molecular-weight medicine, a protein type medicine, a labeling substance, and the like.

Examples of the inhibitory nucleic acid include siRNA, shRNA, miRNA, antisense RNA, and the like.

Examples of low-molecular-weight medicine include a medicine having a molecular weight of approximately 1000 or less. The low-molecular-weight medicine may be, for example, an anticancer agent, a contrast medium, or the like. Examples of anticancer agents include paclitaxel, doxorubicin, cisplatin, gemcitabine, and the like.

Examples of protein type medicines include antibody medicines such as Herceptin, Avastin, and Cyramza.

Examples of labeling substances include quantum dots, gold nanoparticles, magnetic particles, silica nanoparticles, and the like.

The method for synthesizing the drug delivery system of the present embodiment is not particularly limited. As one option, reactive functional groups may be introduced into the drug and the pH-responsive polymer to cause a reaction and bond the two with each other. As another option, a drug that is a protein type medicament may be modified with a pH-responsive polymer by using physical adsorption or bonding reactive functional groups to each other. Alternatively, the pH-responsive polymer may be bonded to the liposome encapsulating the drug by using physical adsorption or bonding reactive functional groups to each other. Otherwise, the surfaces of quantum dots, gold nanoparticles, magnetic particles, silica nanoparticles or the like may be coated by using physical adsorption or bonding reactive functional groups to each other.

In addition, the drug delivery system may form a polymer micelle through the synthesis and self-organization of a block copolymer, or may be in the form of a polymeric vesicle.

The combination of reactive functional groups is not particularly limited, and examples thereof include a combination of an azide group and dibenzocyclooctyne (DBCO), a combination of a succinimide group and an amino group, a combination of a thiol group and a maleimide group, a combination of an azide group and an alkyne group, a combination of a biotin group and a streptavidin group, and the like. In addition, other than the reactive functional group, for example, a bond by a coordination bond between a thiol group and gold may be utilized.

Either one of these combinations may be introduced into the drug and another may be introduced into the pH-responsive polymer to carry out the reaction therebetween. Alternatively, these reactive functional groups may be introduced into the pH-responsive polymer, and the block copolymer may be formed by a polymerization reaction using the reactive functional groups. Alternatively, a pH-responsive polymer having a thiol group may be prepared and introduced into the gold nanoparticle surface.

EXAMPLES

Next, a more detailed description will be given of the present invention by illustrating Experimental Examples, but the present invention is not limited to the following Experimental Examples.

Synthesis of Polymers of Example 1, Comparative Example 1, and Comparative Example 2

Polymers of Example 1, Comparative Example 1, and Comparative Example 2 were synthesized.

(Synthesis of Poly(β-benzyl L-glutamic Acid)

First, Poly(β-benzyl L-glutamic acid) (PBLG) was synthesized. 5.0 g of BLG-N-carboxyanhydride (BLG-NCA) was dissolved in 25 mL of N,N-dimethylformamide (DMF) in an argon atmosphere and 75 mL of dichloromethane (DCM) was added thereto.

38.4 mg of 11-azido-3,6,9-trioxaundecane-1-amine was added to the obtained solution, and the mixture was stirred at room temperature in an argon atmosphere for 2 days. Next, the reaction solution was poured into an excess amount of diethyl ether to reprecipitate the product, recovered, and dried under reduced pressure to obtain 4.0 g of a white solid (yield 95%).

The structure was confirmed by $^1$H NMR analysis and confirmed to be PBLG.

$d_6$-DMSO, Internal standard TMS, δ (ppm): 2.0-2.4 (200H, m, CO—CH—C$\underline{H_2}$—CH$_2$), 2.7 (200H, m, CO—CH—CH$_2$—C$\underline{H_2}$), 3.1-3.7 (16H, m, N$_3$—(C$\underline{H_2}$CH$_2$O)$_3$ —C$\underline{H_2}$—C$\underline{H_2}$), 4.0 (100H, m, CO—C$\underline{H}$—NH), 5.0 (200H, m, C$\underline{H_2}$-Ph), 7.2 (500H, m, CH$_2$—P$\underline{h}$), in which Ph represents a phenyl group.

In addition, the molecular weight was calculated by size-exclusion chromatography (SEC) analysis, and the average degree of polymerization was found to be 100 (Mw/Mn=1.2).

(Synthesis of PGlu (EDA), PGlu (DET) and PGlu (DPT))

PGlu (EDA), PGlu (DET), and PGlu (DPT) were synthesized by an aminolysis reaction with respect to the benzyl group of the side chain of PBLG.

First, 1 g of PBLG and 2.7 g of 2-hydroxypyridine were dissolved in 45 mL of N-methylpyrrolidone (NMP). 19 g of ethylenediamine (EDA) was added to the obtained solution, the reaction solution was neutralized by dialysis with 0.3 M hydrochloric acid, followed by dialysis with respect to 0.01 M hydrochloric acid and further dialysis with respect to pure water. The dialyzed aqueous solution was lyophilized to obtain a white solid (PGlu (EDA)) as a product (0.8 g, yield 81%).

In the same manner, PGlu (DET) and PGlu (DPT) were obtained by reactions of diethylenetriamine (DET) and dipropylenediamine (DPT) with respect to PBLG, respectively. The obtained PGlu (EDA), PGlu (DET), and PGlu (DPT) were each confirmed to have the desired structure by $^1$H NMR analysis.

PGlu (EDA): D$_2$O, Internal standard TSP, δ (ppm): 1.9-2.2 (200H, m, CO—CH—C$\underline{H_2}$—CH$_2$), 2.4 (200H, m, CO—CH—CH$_2$—C$\underline{H_2}$), 3.1-3.7 (416H, m, N$_3$—(C$\underline{H_2}$CH$_2$O)$_3$—C$\underline{H_2}$—C$\underline{H_2}$, CONH—C$\underline{H_2}$—C$\underline{H_2}$—NH$_2$), 4.3 (100H, m, CO—C$\underline{H}$—NH)

PGlu (DET): D$_2$O, Internal standard TSP, δ (ppm): 1.9-2.2 (200H, m, CO—CH—C$\underline{H_2}$—CH$_2$), 2.4 (200H, m, CO—CH—CH$_2$—C$\underline{H_2}$), 2.9-3.7 (816H, m, N$_3$—(C$\underline{H_2}$CH$_2$O)$_3$—C$\underline{H_2}$—C$\underline{H_2}$, CONH—C$\underline{H_2}$—C$\underline{H_2}$—NH—C$\underline{H_2}$—C$\underline{H_2}$—NH$_2$), 4.3 (100H, m, CO—C$\underline{H}$—NH)

PGlu (DPT): D$_2$O, Internal standard TSP, δ (ppm): 1.9-2.2 (600H, m, CO—CH—C$\underline{H_2}$—CH$_2$, CONH—CH$_2$—C$\underline{H_2}$—CH$_2$—NH—CH$_2$—C$\underline{H_2}$—CH$_2$—NH$_2$), 2.4 (200H, m, CO—CH—CH$_2$—C$\underline{H_2}$), 3.1-3.7 (816H, m, N$_3$—(C$\underline{H_2}$CH$_2$O)$_3$—C$\underline{H_2}$—C$\underline{H_2}$, CONH—C$\underline{H_2}$—CH$_2$—CH$_2$—NH—C$\underline{H_2}$—CH$_2$—C$\underline{H_2}$—NH$_2$), 4.3 (100H, m, CO—C$\underline{H}$—NH)

(Synthesis of PGlu (EDA-Car), PGlu (DET-Car), and PGlu (DPT-Car)

Carboxyl groups were introduced into the primary amines of the side chain of PGlu (EDA), PGlu (DET), and PGlu (DPT) by a Michael reaction with acrylic acid. First, 100 mg of PGlu (EDA) was dissolved in 30 mL of a 0.5 M sodium carbonate aqueous solution and 8.5 mL of acrylic acid was added thereto. After the pH of the reaction solution was adjusted to 9 to 10 using a 5 M aqueous sodium hydroxide solution, the mixture was stirred at room temperature for 1 week. The obtained reaction solution was dialyzed with respect to 0.01 M hydrochloric acid, followed by pure water, and lyophilized to obtain the polymer of Comparative Example 1 (may be referred to below as "PGlu (EDA-Car)") as a milky white solid (95 mg, 95% yield).

In the same manner, the polymer of Example 1 (may be referred to below as "PGlu (DET-Car)") and the polymer of Comparative Example 2 (may be referred to below as "PGlu (DPT-Car)") were obtained. Each of the polymers of Example 1, Comparative Example 1, and Comparative Example 2 were confirmed to have a desired structure by $^1$H NMR analysis.

PGlu (EDA-Car): $D_2O$, Internal standard TSP, δ (ppm): 1.9-2.2 (200H, m, CO—CH—C$\underline{H}_2$—C$\underline{H}_2$), 2.4-2.6 (400H, m, CO—CH—CH$_2$—C$\underline{H}_2$—CONH—C$\underline{H}_2$—C$\underline{H}_2$—NH—C$\underline{H}_2$—C$\underline{H}_2$—COOH), 3.0-3.7 (616H, m, N$_3$—(C$\underline{H}_2$C$\underline{H}_2$O)$_3$—C$\underline{H}_2$—C$\underline{H}_2$, CONH—C$\underline{H}_2$—C$\underline{H}_2$—NH—C$\underline{H}_2$—C$\underline{H}_2$—COOH), 4.3 (100H, m, CO—C$\underline{H}$—NH)

PGlu (DET-Car): $D_2O$, Internal standard TSP, δ (ppm): 1.9-2.2 (200H, m, CO—CH—C$\underline{H}_2$—C$\underline{H}_2$), 2.4 (200H, m, CO—CH—CH$_2$—C$\underline{H}_2$), 2.6-3.7 (1216H, m, N$_3$—(C$\underline{H}_2$C$\underline{H}_2$O)$_3$—C$\underline{H}_2$—C$\underline{H}_2$, CONH—C$\underline{H}_2$—C$\underline{H}_2$—NH—C$\underline{H}_2$—C$\underline{H}_2$—NH—C$\underline{H}_2$—C$\underline{H}_2$—COOH), 4.3 (100H, m, CO—C$\underline{H}$—NH)

PGlu (DPT-Car): $D_2O$, Internal standard TSP, δ (ppm): 1.9-2.2 (600H, m, CO—CH—C$\underline{H}_2$—CH$_2$, CONH—CH$_2$—C$\underline{H}_2$—CH$_2$—NH—CH$_2$—C$\underline{H}_2$—CH$_2$—NH), 2.4 (200H, m, CO—CH—CH$_2$—C$\underline{H}_2$), 2.7 (200H, m, NH—C$\underline{H}_2$—CH$_2$—COOH), 3.1-3.7 (1016H, m, N$_3$—(C$\underline{H}_2$C$\underline{H}_2$O)$_3$—C$\underline{H}_2$—C$\underline{H}_2$, CONH—C$\underline{H}_2$—CH$_2$—CH$_2$—NH—C$\underline{H}_2$—CH$_2$—C$\underline{H}_2$—NH—C$\underline{H}_2$—CH$_2$—CO OH), 4.3 (100H, m, CO—C$\underline{H}$—NH)

The chemical formula of the polymer of Example 1 is shown in Formula (8). The polymer of Example 1 has polyglutamic acid as a biocompatible polymer and is a polymer in which a group which has an ethylenediamine structure is bonded as a group which is electrically neutral under pH environments of more than 7 and which changes to be cationic at pH 7 or less.

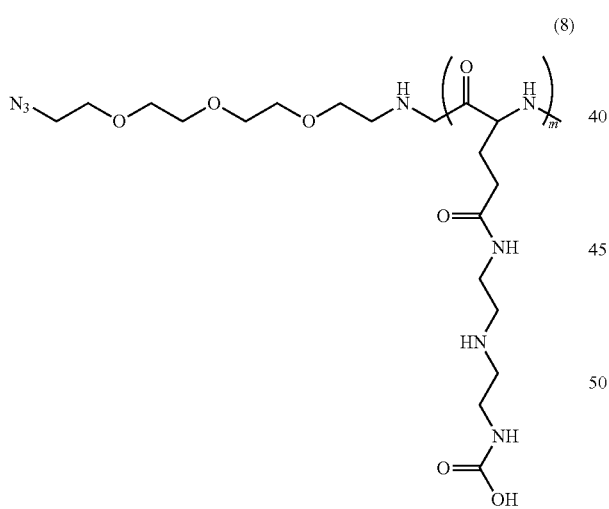

(8)

[in Formula (8), the average value of m is 100.]

Next, the chemical formula of the polymer of Comparative Example 1 is shown in Formula (9). The polymer of Comparative Example 1 is a polymer having polyglutamic acid as a biocompatible polymer and having one secondary amine, and is electrically neutral in both of a pH environment (pH 7.4) corresponding to normal tissue and a pH environment (pH of approximately 6.5 or lower) corresponding to the periphery of tumor tissue.

The charge of the secondary amine moiety and the carboxyl group moiety of the polymer of Comparative Example 1 is shown in Formula (10). As shown in Formula (10), one secondary amine introduced into the polymer of Comparative Example 1 has one positive charge under both of pH environments (pH 7.4) corresponding to normal tissue and pH environments (pH of approximately 6.5 or lower) corresponding to the periphery of tumor tissue.

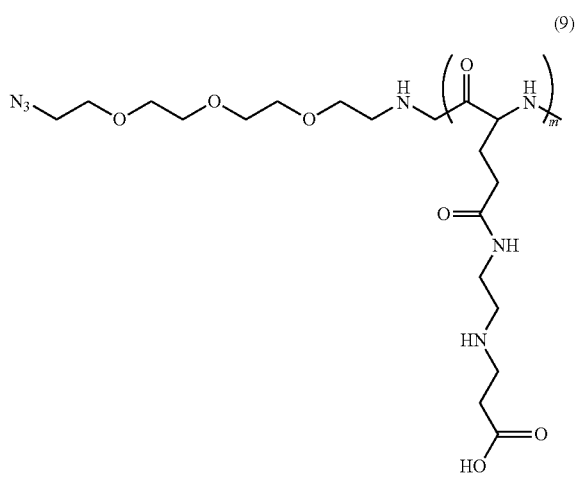

(9)

[in Formula (9), the average value of m is 100.]

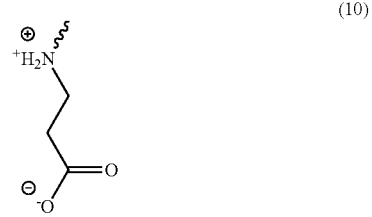

(10)

Next, the chemical formula of the polymer of Comparative Example 2 is shown in Formula (11). The polymer of Comparative Example 2 is a polymer having polyglutamic acid as a biocompatible polymer and having a propylene diamine structure and is cationic in both of a pH environment (pH 7.4) corresponding to normal tissue and a pH environment (pH of approximately 6.5 or lower) corresponding to the periphery of tumor tissue.

The charge of the propylene diamine structure moiety and the carboxyl group moiety of the polymer of Comparative Example 2 is shown in Formula (12). As shown in Formula (12), the propylene diamine structure has two positive charges in both of a pH environment (pH 7.4) corresponding to normal tissue and a pH environment (pH of approximately 6.5 or lower) corresponding to the periphery of tumor tissue.

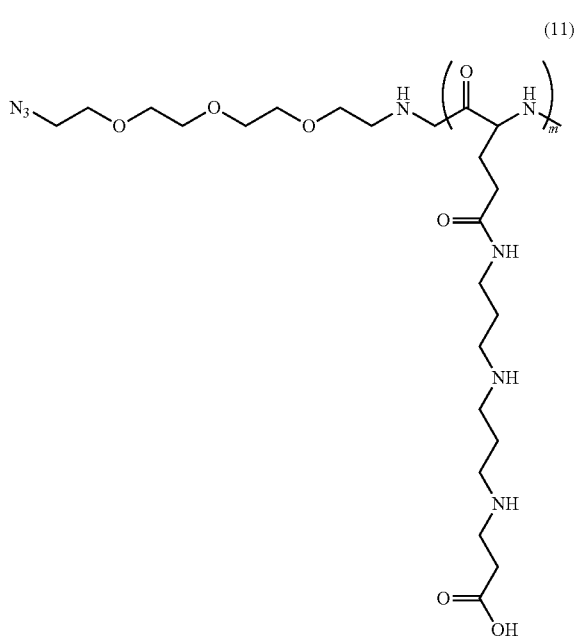

[in Formula (11), the average value of m is 100.]

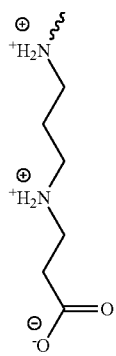

Experimental Example 1

(Interaction Test of Polymer and Anionic Sugar Chain)

In general, the surface of the cell membrane is covered with anionic sugar chains. Here, the pH-dependent interaction between the polymer of Example 1 and Comparative Example 1 and the anionic sugar chain was investigated. Heparin was used as the anionic sugar chain.

First, each polymer was labeled with Cy3, which is a fluorescent material. Next, mixed solutions of 300 nM of each polymer and 100 μg/mL of heparin were prepared, and the diffusion coefficient of each polymer was measured using fluorescence correlation spectroscopy (FCS) under various conditions of pH (model "LSM 710", Carl-Zeiss). A decrease in the diffusion coefficient of the polymer indicates that heparin and the polymer interacted to form aggregates. Conditions of pH of pH 6.0, 6.5 and 7.0 were prepared with an MES buffer solution (50 mM) and conditions of pH of pH 7.4 and 8.0 were prepared with a HEPES buffer solution (50 mM).

FIG. 1 is a graph showing measurement results by FCS. As a result, it was found that the polymer of Example 1 exhibited no interaction with heparin under conditions of pH corresponding to the peripheral environment of the normal tissue (pH approximately 7.4), and aggregates with heparin were formed (the diffusion coefficient decreased) under weakly acidic conditions corresponding to the peripheral environment of the tumor (pH approximately 6.5). In contrast, no interaction with heparin was observed in the polymer of Comparative Example 1 even when the conditions of pH were changed.

From these results, it was shown that the polymer of Example 1 does not interact with the cells of normal tissue, but specifically adsorbs to cell membranes of tumor tissue cells and promotes incorporation into cells.

Experimental Example 2

(Investigation of Incorporation of Polymer into Cell)

The polymer of Example 1 and Comparative Example 1 was brought into contact with human lung cancer cells A549 under various conditions of pH to investigate whether the polymer was incorporated into cells or not.

First, 100,000 A549 cells per well were seeded in a 6-well plate and incubated overnight in an RPMI medium with 10% fetal bovine serum (FBS). Next, the medium was replaced with a pH 7.4 buffer solution (10 mM HEPES, 150 mM NaCl, 10% FBS), a pH 6.5 buffer solution (10 mM phosphate buffer solution, 150 mM NaCl, 10% FBS) or a pH 5.5 buffer solution (10 mM MES, 150 mM NaCl, 10% FBS).

Next, each Cy3-labeled polymer was added to make a final concentration of 500 nM and incubated at 37° C. for 1 hour. Next, A549 cells were subjected to a rinsing treatment with a buffer solution not including FBS, recovered by further performing a trypsinization treatment, analyzed by flow cytometry (type "Guava easyCyte 6-2 L", Merck Millipore), and the fluorescence intensity of Cy3 incorporated into the A549 cells was measured.

Figure 2:
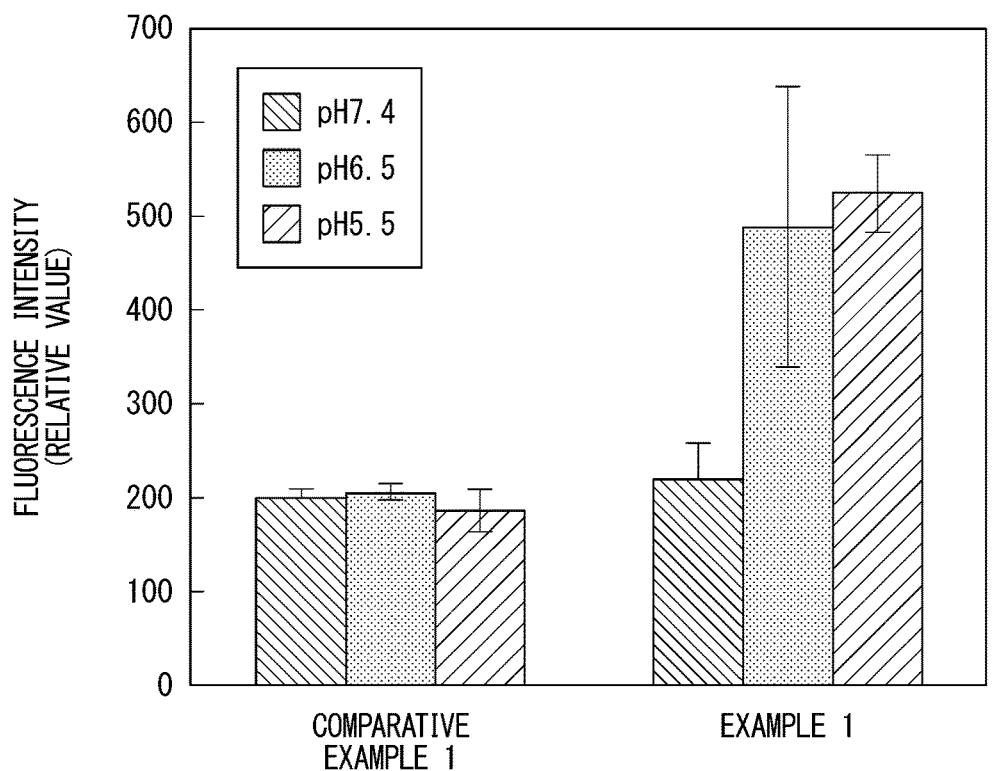
FIG. 2 is a graph showing results of measuring polymer incorporation into cells by flow cytometry in Experimental Example 2.

FIG. 2 is a graph showing the flow cytometry results. As a result, for the polymer of Comparative Example 1, no change in cell incorporation was observed in a pH range of 7.4 to 5.5. In contrast, it was found that the polymer of Example 1 had an increased incorporation into the cells when the pH was lowered to 6.5 or less.

From these results, it was found that, under the conditions of pH corresponding to the peripheral environment of the normal tissue (pH approximately 7.4), both the polymer of Example 1 and the polymer of Comparative Example 1 exhibited a similar incorporation into cells.

On the other hand, it was found that no change was observed in the incorporation of the polymer of Comparative Example 1 into the cells under the conditions of pH of weakly acidic conditions (pH approximately 6.5) or less corresponding to the peripheral environment of the tumor, while incorporation into the cells was increased in the polymer of Example 1.

That is, it was confirmed that the polymer of Example 1 being electrically neutral under conditions of pH close to neutral suppresses incorporation into the cells of normal tissue and that the pH being selectively cationic under weakly acidic or lower pH conditions increases the incorporation into tumor tissue cells.

Experimental Example 3

(Cell Membrane Damage Test)

Cationic substances often disrupt the cell membrane by strongly interacting with the cell membrane and may exhibit cytotoxicity. Therefore, the cell membrane damage test of the polymers of Example 1, Comparative Example 1, and Comparative Example 2 was performed. Specifically, a lactate dehydrogenase (LDH) activity test was carried out by bringing each polymer into contact with human lung cancer cells A549 under various conditions of pH.

First, 100,000 A549 cells per well were seeded in a 6-well plate and incubated overnight in an RPMI medium with 10% fetal bovine serum (FBS). Next, the medium was replaced with a pH 7.4 buffer solution (10 mM HEPES, 150 mM NaCl, 10% FBS), a pH 6.5 buffer solution (10 mM phosphate buffer solution, 150 mM NaCl, 10% FBS) or a pH 5.5 buffer solution (10 mM MES, 150 mM NaCl, 10% FBS).

Next, each polymer of each concentration was added and incubated at 37° C. for 1.5 hours. Next, the amount of LDH leaking from the inside of the cells was measured using an LDH assay kit (Dojindo), and the damage to the cell membrane was quantified. This is based on the fact that the polymer has cytoplasmic toxicity and the LDH in the cells leaks out of the cells in cases where the cell membrane is damaged. Measuring the extracellular LDH activity makes it possible to evaluate the cytoplasmic toxicity of each polymer.

Figure 3:
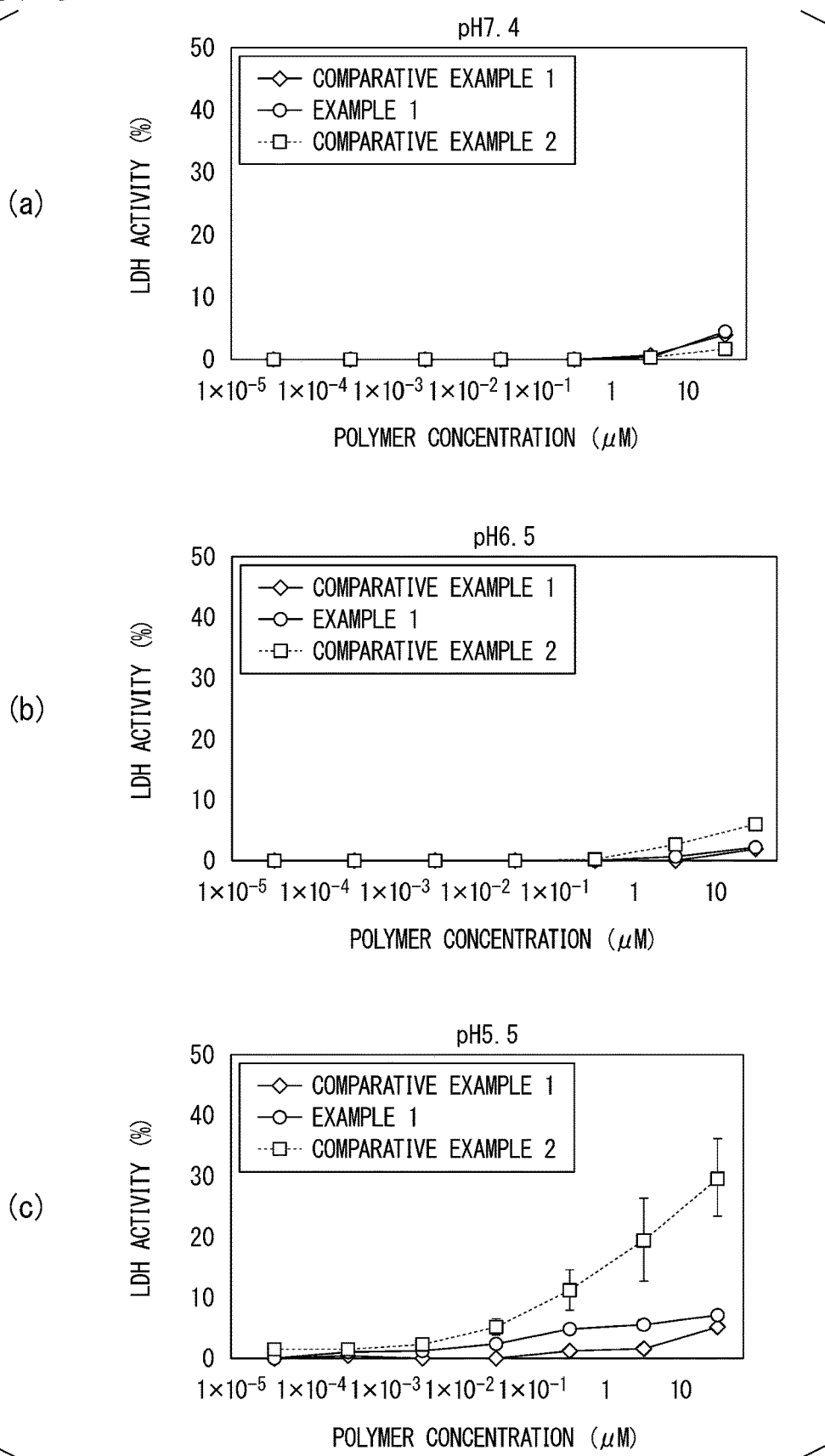
FIGS. 3(a) to 3(c) are graphs showing results of a lactate dehydrogenase (LDH) activity test in Experimental Example 3.

FIG. 3(a) to (c) are graphs showing the results of the LDH activity test. FIG. 3(a) is a test result at pH 7.4, FIG. 3(b) is a test result at pH 6.5, and FIG. 3(c) is a test result at pH 5.5.

As a result, it was found that the polymers of Example 1 and Comparative Example 1 did not exhibit obvious LDH activity at any pH.

From these results, it was found that, although the polymer of Example 1 exhibited adsorption to the cell membrane and incorporation into the cell in response to a weakly acidic to acidic pH, it was a polymer with high biocompatibility which does not cause damage to the cell membrane.

In addition, the results of the polymer of Comparative Example 1 were consistent with the results of Experimental Examples 1 and 2 and show no pH-responsiveness, no interaction with cells under any condition of pH, and little incorporation into the cells.

In addition, it was found that the polymer of Comparative Example 2 had an increased LDH activity as the pH was lowered. From these results, it was found that the polymer of Comparative Example 2 exhibits cytotoxicity under acidic conditions.

Experimental Example 4

(Cytotoxicity Test)

Cytotoxicity tests were carried out on the polymers of Example 1, Comparative Example 1, and Comparative Example 2. Specifically, various concentrations of each polymer were added to a medium of human lung cancer cells A549 under various conditions of pH and cultured for 1 day to measure cell viability.

First, 5,000 A549 cells per well were seeded in a 96-well plate and incubated overnight in an RPMI medium with 10% FBS. Next, the medium was replaced with an ordinary RPMI medium (pH 7.4) and an RPMI medium adjusted to pH 6.7 and various concentrations of each polymer were added thereto and cultured at 37° C. for 1 day to measure the cell viability. A CCK-8 kit (Dojindo) was used to measure cell viability.

Figure 4:
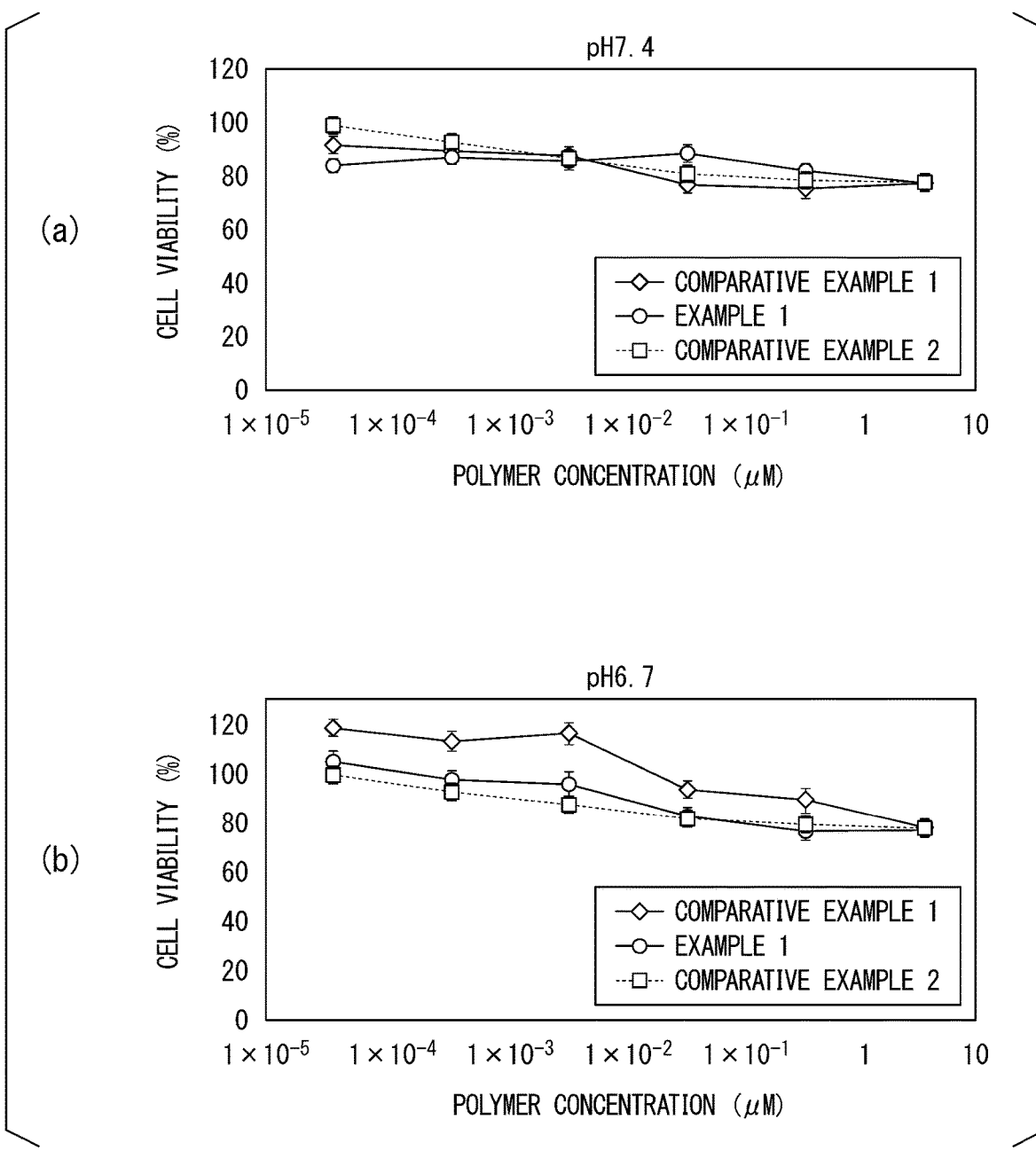
FIGS. 4(a) and 4(b) are graphs showing results of the cytotoxicity test in Experimental Example 4.

FIGS. 4(a) and (b) are graphs showing the results of the cytotoxicity test. FIG. 4(a) shows the result at pH 7.4 and FIG. 4(b) shows the result at pH 6.7. As a result, it was found that neither polymer exhibits obvious cytotoxicity regardless of pH or concentration.

Experimental Example 5

(Blood Retention Test and Tumor Accumulation Test)

Blood retention and accumulation in tumors were examined in vivo using nanoparticles coated with polymers of Example 1, Comparative Example 1, and Comparative Example 2.

First, quantum dots, which are nanoparticle (drug) models, were coated with the polymers of Example 1, Comparative Example 1, and Comparative Example 2. In addition, for comparative purposes, quantum dots coated using a polyethylene glycol (PEG) used in the related art were also prepared in the same manner. The quantum dots coated with the polymer of Example 1 may be referred to as "quantum dots of Example 1". Similarly, the quantum dots coated with the polymer of Comparative Example 1 may be referred to as "quantum dots of Comparative Example 1", and the quantum dots coated with the polymer of Comparative Example 2 may be referred to as "quantum dots of Comparative Example 2".

Next, CT26 cells, which are a mouse colon cancer cell line, were transplanted subcutaneously into BALB/c mice (female, 5 weeks old) to prepare mouse cancer models. When the tumor tissue size reached 50 to 100 mm$^3$, 200 pmol of each quantum dot was administered to the tail vein. After that, blood collection was performed over time, and, after 48 hours, the mice were euthanized and the tumor tissue was excised.

Next, each collected sample was treated at 180° C. in 90% nitric acid. The amount of cadmium derived from the quantum dots included in the obtained aqueous solution was measured with ICP-MS (type "Agilent 7700 ICP-MS", Agilent Technologies) to quantify the amounts of each quantum dot and evaluation was carried out on the blood retention and accumulation in the tumor tissue of each quantum dot.

Figure 5:
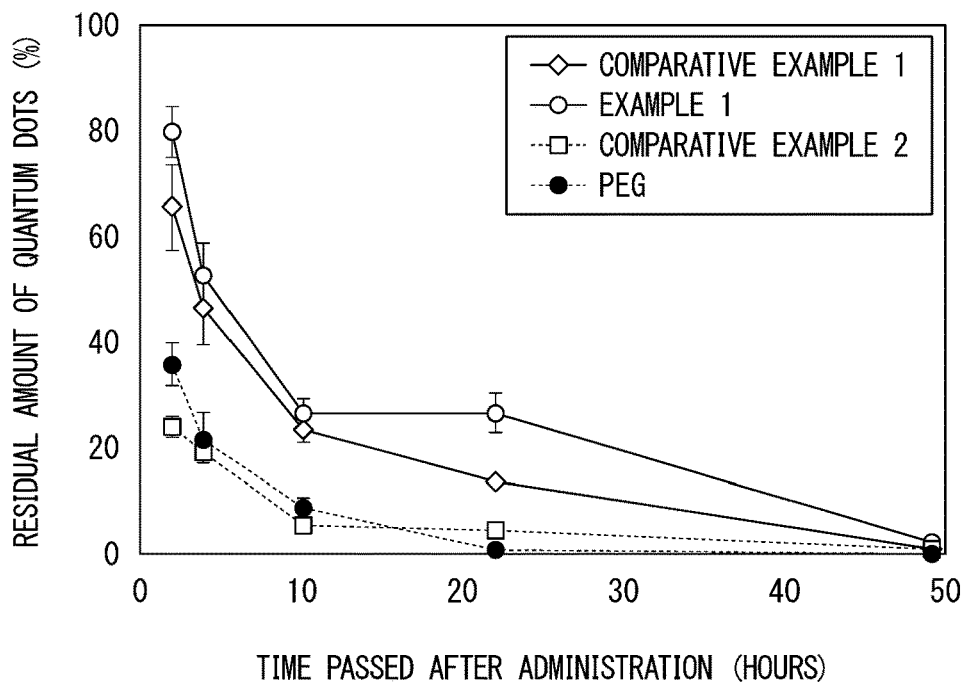
FIG. 5 is a graph showing results of measuring quantum dots remaining in blood over time in Experimental Example 5.

FIG. 5 is a graph showing the results of measuring the residual amount of each quantum dot in the blood over time. As a result, it was found that the quantum dots of Example 1 and Comparative Example 1 showed equivalent blood retention. This result shows that these quantum dots have equivalent stealth properties in vivo.

On the other hand, it was found that the quantum dots of Comparative Example 2 exhibited lower blood retention as compared with the quantum dots of Example 1 and Comparative Example 1. Since the polymer of Comparative Example 2 is cationic under weakly basic to acidic pH conditions, the polymer interacts with components in the blood and normal tissue, and it is considered that the disappearance from the blood is fast.

In addition, the quantum dots of Example 1 and Comparative Example 1 exhibited higher blood retention as compared with quantum dots coated with PEG used in the related art. This result shows that the polymers of Example 1 and Comparative Example 1 have superior stealth properties than PEG in vivo.

Figure 6:
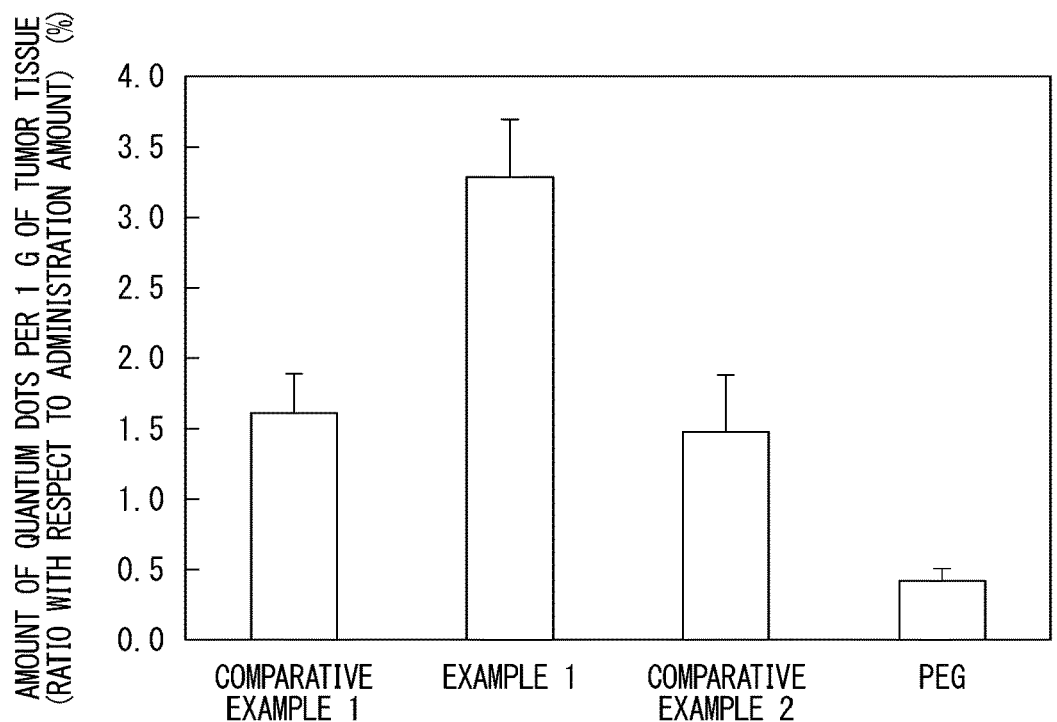
FIG. 6 is a graph showing results of quantifying quantum dots in excised tumor tissue in Experimental Example 5.

FIG. 6 is a graph showing quantitative results of quantum dots in excised tumor tissue. As a result, although the quantum dots of Example 1 and the quantum dots of Comparative Example 1 exhibited equivalent blood retention, it was found that the quantum dots of Example 1 had higher accumulation in tumor tissue than the quantum dots of Comparative Example 1. This result indicates that the stealth property in the blood is equivalent in the quantum dots of Example 1 and Comparative Example 1, but in the weakly acidic environment in the periphery of the tumor tissue, the polymer of Example 1 changes to be cationic such that the interaction of the quantum dots of Example 1 with tumor tissue cells increases and incorporation into the cells is promoted.

In addition, the accumulation of the quantum dots of Comparative Example 2 in the tumor tissue was similar to that of the quantum dots of Comparative Example 1. Furthermore, the accumulation of quantum dots coated with PEG used in the related art in tumor tissue was remarkably lower than the accumulation amounts of Comparative Example 1 and Comparative Example 2 in tumor tissue.

Synthesis of Polymer of Example 2

The polymer of Example 2 was synthesized. The polymer of Example 2 was PGlu (DET-Car) with an average degree of polymerization of 75.

(Synthesis of Poly(β-benzyl L-glutamic Acid)

First, Poly(β-benzyl L-glutamic acid) (PBLG) was synthesized. 5.0 g of BLG-N-carboxyanhydride (BLG-NCA) was dissolved in 10 mL of N,N-dimethylformamide (DMF) in an argon atmosphere and 40 mL of dichloromethane (DCM) was added thereto.

40.0 mg of 11-azido-3,6,9-trioxaundecane-1-amine was added to the obtained solution and stirred overnight at room temperature in an argon atmosphere. Next, the reaction solution was poured into an excess amount of diethyl ether to reprecipitate the product, recovered, and dried under reduced pressure to obtain 3.9 g of a white solid (yield: 79%).

The structure was confirmed by $^1$H NMR analysis and confirmed to be PBLG.

$d_6$-DMSO, Internal standard TMS, δ (ppm): 2.0-2.4 (150H, m, CO—CH—C$\underline{H_2}$—CH$_2$), 2.7 (150H, m, CO—CH—CH$_2$—C$\underline{H_2}$), 3.1-3.7 (16H, m, N$_3$—(C$\underline{H_2}$CH$_2$O)$_3$—C$\underline{H_2}$—C$\underline{H_2}$), 4.0 (75H, m, CO—C$\underline{H}$—NH), 5.0 (150H, m, C$\underline{H_2}$-Ph), 7.2 (375H, m, CH$_2$—$\underline{Ph}$), in which Ph represents a phenyl group.

In addition, the molecular weight was calculated by size-exclusion chromatography (SEC) analysis, and it was found that the average degree of polymerization was 75 (Mw/Mn=1.2).

(Synthesis of PGlu (DET))

PGlu (DET) was synthesized by an aminolysis reaction on the benzyl group of the side chain of PBLG. First, 660 mg of PBLG and 1.4 g of 2-hydroxypyridine were dissolved in 48 mL of N-methylpyrrolidone (NMP). 15.4 g of diethylenetriamine (DET) was added to the obtained solution and the mixture was stirred at room temperature for 4 days. The reaction solution was neutralized by dialysis with 0.3 M hydrochloric acid, followed by dialysis with respect to 0.01 M hydrochloric acid and further dialysis with respect to pure water. The dialyzed aqueous solution was lyophilized to obtain a white solid (PGlu (DET)) as a product (0.64 g, yield 97%). It was confirmed by $^1$H NMR analysis that the obtained PGlu (DET) was a target structure.

PGlu (DET): D$_2$O, Internal standard TSP, δ (ppm): 1.9-2.2 (150H, m, CO—CH—C$\underline{H_2}$—CH$_2$), 2.4 (150H, m, CO—CH—CH$_2$—C$\underline{H_2}$), 2.9-3.7 (616H, m, N$_3$—(CH$_2$CH$_2$O)$_3$—C$\underline{H_2}$—C$\underline{H_2}$, CONH—C$\underline{H_2}$—C$\underline{H_2}$—NH—C$\underline{H_2}$—C$\underline{H_2}$—NH$_2$), 4.3 (75H, m, CO—C$\underline{H}$—NH)

(Synthesis of PGlu (DET-Car))

A carboxyl group was introduced into the primary amine in the side chain of PGlu (DET) by a Michael reaction with acrylic acid. First, 200 mg of PGlu (DET) was dissolved in 60 mL of a 0.5 M sodium carbonate aqueous solution and 2.2 mL of acrylic acid was added thereto. The pH of the reaction solution was adjusted to 9 to 10 with a 5 M aqueous sodium hydroxide solution, and then the mixture was stirred at room temperature for 1 week. The obtained reaction solution was dialyzed with respect to 0.01 M hydrochloric acid, followed by pure water, and lyophilized to obtain PGlu (DET-Car) (may be referred to below as "polymer of Example 2") as a milky white solid (210 mg, yield 82%). The target structure was confirmed by $^1$H NMR analysis.

PGlu (DET-Car): D$_2$O, Internal standard TSP, δ (ppm): 1.9-2.2 (150H, m, CO—CH—C$\underline{H_2}$—CH$_2$), 2.4 (150H, m, CO—CH—CH$_2$—C$\underline{H_2}$), 2.6-3.7 (916H, m, N$_3$—(CH$_2$CH$_2$O)$_3$—C$\underline{H_2}$—C$\underline{H_2}$, CONH—C$\underline{H_2}$—C$\underline{H_2}$—NH—C$\underline{H_2}$—C$\underline{H_2}$—NH—C$\underline{H_2}$—C$\underline{H_2}$—COOH), 4.3 (75H, m, CO—C$\underline{H}$—NH)

Synthesis of Polymer of Example 3

The polymer of Example 3 was synthesized. The polymer of Example 3 was PGlu (DET-Car) with an average degree of polymerization of 112.

(Synthesis of Poly(β-benzyl L-glutamic acid)

First, Poly(β-benzyl L-glutamic acid) (PBLG) was synthesized. 3.0 g of BLG-N-carboxyanhydride (BLG-NCA) was dissolved in 6 mL of N,N-dimethylformamide (DMF) in an argon atmosphere and an additional 24 mL of dichloromethane (DCM) was added thereto.

19.1 mg of 11-azido-3, 6, 9-trioxaundecane-1-amine was added to the obtained solution and stirred at room temperature for 24 hours in an argon atmosphere. Next, the reaction solution was poured into an excess amount of diethyl ether to reprecipitate the product, recovered, and dried under reduced pressure to obtain 2.2 g of a white solid (yield: 85%).

The structure was confirmed by $^1$H NMR analysis and confirmed to be PBLG.

$d_6$-DMSO, Internal standard TMS, δ (ppm): 2.0-2.4 (224H, m, CO—CH—C$\underline{H_2}$—CH$_2$), 2.7 (224H, m, CO—CH—CH$_2$—C$\underline{H_2}$), 3.1-3.7 (16H, m, N$_3$—(C$\underline{H_2}$CH$_2$O)$_3$—C$\underline{H_2}$—C$\underline{H_2}$), 4.0 (112H, m, CO—C$\underline{H}$—NH), 5.0 (224H, m, C$\underline{H_2}$-Ph), 7.2 (560H, m, CH$_2$—$\underline{Ph}$), in which Ph represents a phenyl group.

In addition, the molecular weight was calculated by size-exclusion chromatography (SEC) analysis, and it was found that the average degree of polymerization was 112 (Mw/Mn=1.2).

(Synthesis of PGlu (DET))

PGlu (DET) was synthesized by an aminolysis reaction on the benzyl group of the side chain of PBLG First, 500 mg of PBLG and 1.0 g of 2-hydroxypyridine were dissolved in 14 mL of N-methylpyrrolidone (NMP). 12.4 g of diethylenetriamine (DET) was added to the obtained solution and the mixture was stirred at room temperature for 4 days. The reaction solution was neutralized by dialysis with 0.3 M hydrochloric acid, followed by dialysis with respect to 0.01 M hydrochloric acid and further dialysis with respect to pure water. The dialyzed aqueous solution was lyophilized to obtain a white solid (PGlu (DET)) as a product (0.49 g, yield 86%). It was confirmed by $^1$H NMR analysis that the obtained PGlu (DET) was a target structure.

PGlu (DET): D$_2$O, Internal standard TSP, δ (ppm): 1.9-2.2 (224H, m, CO—CH—C$\underline{H_2}$—CH$_2$), 2.4 (224H, m, CO—CH—CH$_2$—CH$_2$), 2.9-3.7 (912H, m, N$_3$—(CH$_2$CH$_2$O)$_3$—CH$_2$—CH$_2$, CONH—CH$_2$—CH$_2$—NH—CH$_2$—CH$_2$—NH$_2$), 4.3 (112H, m, CO—CH—NH)

(Synthesis of PGlu (DET-Car))

A carboxyl group was introduced into the primary amine in the side chain of PGlu (DET) by a Michael reaction with acrylic acid. First, 200 mg of PGlu (DET) was dissolved in 25 mL of a 0.5 M sodium carbonate aqueous solution and 3.2 mL of acrylic acid was added thereto. The pH of the reaction solution was adjusted to 9 to 10 with a 5 M aqueous sodium hydroxide solution, and then the mixture was stirred at room temperature for 1 week. The obtained reaction solution was dialyzed with respect to 0.01 M hydrochloric acid, followed by pure water, and lyophilized to obtain PGlu (DET-Car) (may be referred to below as "polymer of Example 3")) as a milky white solid (213 mg, 83% yield). The target structure was confirmed by $^1$H NMR analysis.

PGlu (DET-Car): D$_2$O, Internal standard TSP, δ (ppm): 1.9-2.2 (224H, m, CO—CH—CH$_2$—CH$_2$), 2.4 (224H, m, CO—CH—CH$_2$—CH$_2$), 2.6-3.7 (1360H, m, N$_3$—(CH$_2$CH$_2$O)$_3$—CH$_2$—CH$_2$, CONH—CH$_2$—CH$_2$—NH—CH$_2$—CH$_2$—NH—CH$_2$—CH$_2$—COOH), 4.3 (112H, m, CO—CH—NH)

Synthesis of Polymer of Example 4

The polymer of Example 4 (may be referred to below as "PGlu (DET-Sul)") was synthesized.

(Synthesis of PGlu (DET-Sul))

A sulfo group was introduced into a primary amine in the side chain of pGlu (DET) (average degree of polymerization 112) synthesized in the same manner as in Example 3 by a Michael reaction with vinyl sulfonic acid. First, 200 mg of PGlu (DET) was dissolved in 25 mL of a 0.5 M sodium carbonate aqueous solution and 6.1 g of sodium vinylsulfonate was added thereto. The pH of the reaction solution was adjusted to 9 to 10 with a 5 M aqueous sodium hydroxide solution, and then the mixture was stirred at room temperature for 2 weeks. PGlu (DET-Sul) (may be referred to below as "polymer of Example 4") was obtained as a pale orange solid (213 mg, 78% yield) by dialyzing the obtained reaction solution with 0.01 M hydrochloric acid, followed by pure water and lyophilization. The target structure was confirmed by $^1$H NMR analysis.

PGlu (DET-Sul): D$_2$O, Internal standard TSP, δ (ppm): 1.9-2.2 (224H, m, CO—CH—CH$_2$—CH$_2$), 2.4 (224H, m, CO—CH—CH$_2$—CH$_2$), 3.0-3.7 (1136H, m, N$_3$—(CH$_2$CH$_2$O)$_3$—CH$_2$—CH$_2$, CONH—CH$_2$—CH$_2$—NH—CH$_2$—CH$_2$—NH—CH$_2$—CH$_2$—SO$_3$H), 3.9 (224H, m, NH—CH$_2$—CH$_2$—SO$_3$H), 4.3 (112H, m, CO—CH—NH)

The chemical formula of the polymer of Example 4 is shown in Formula (13). The polymer of Example 4 has polyglutamic acid as a biocompatible polymer and a polymer in which a group having an ethylenediamine structure is bonded as a group which is electrically neutral under pH environment of more than 7 and changes to be cationic at pH of 7 or less.

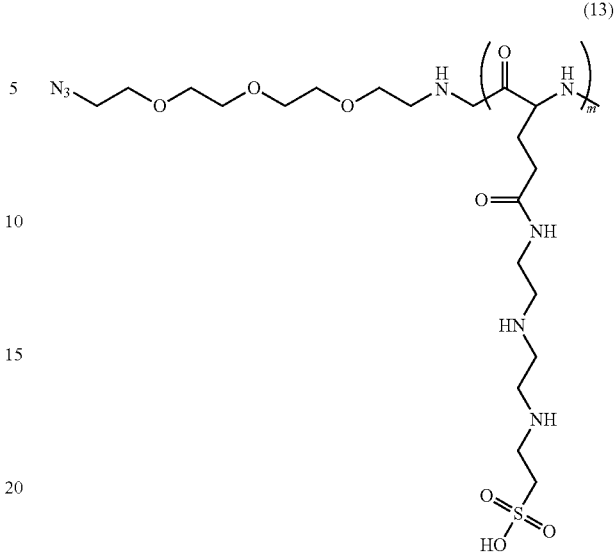

[in Formula (13), the average value of m is 112.]

Experimental Example 6

(Measurement of pKa of Polymer of Example 1)

The pKa of the polymer of Example 1 was measured. As described above, the polymer of Example 1 was PGlu (DET-Car) having an average degree of polymerization of 100.

5 mg of PGlu (DET-Car) was dissolved in 2 mL of 150 mM NaCl 0.1 M HCl and a titration test was carried out with 150 mM of NaCl 0.01 M NaOH. For the titration device, model "COM-1750 M" (Hiranuma Sangyo) was used. As a result, it was found that the polymer of Example 1 had a pKa of 4.3 (derived from a carboxylic acid), 6.0 (derived from ethylenediamine), and 8.8 (derived from ethylenediamine).

Experimental Example 7

(Measurement of pKa of Polymer of Example 4)

The pKa of the polymer of Example 4 was measured. As described above, the polymer of Example 4 was PGlu (DET-Sul) with an average degree of polymerization of 112.

5 mg of PGlu (DET-Sul) was dissolved in 2 mL of 150 mM NaCl 0.1 M HCl and a titration test was carried out with 150 mM of NaCl 0.01 M NaOH. For the titration device, the model "COM-1750 M" (Hiranuma Sangyo) was used. As a result, it was found that the polymer of Example 4 had a pKa of 6.4 (derived from ethylenediamine) and 8.9 (derived from ethylenediamine).

Experimental Example 8

(Interaction Test of Polymer of Example 3 and Anionic Sugar Chain)

As described above in Experimental Example 1, in general, the surface of the cell membrane is covered with anionic sugar chains. Therefore, the pH-dependent interaction between the polymer of Example 3 and the anionic sugar chain was investigated. Heparin was used as the anionic sugar chain. As described above, the polymer of Example 3 was PGlu (DET-Car) having an average degree of polymerization of 112.

First, PGlu (DET-Car) was labeled with Cy3, which is a fluorescent substance. Next, a mixed solution of 200 nM of a polymer and 100 μg/mL heparin was prepared and the diffusion coefficient of the polymer was measured using fluorescence correlation spectroscopy (FCS) under various conditions of pH (model "LSM 710" Carl-Zeiss). A decrease in the diffusion coefficient of the polymer indicates that heparin and the polymer interacted to form aggregates. Conditions of pH of pH 6.0, 6.5 and 7.0 were prepared with an MES buffer solution (50 mM) and conditions of pH of pH 7.4 and 8.0 were prepared with a HEPES buffer solution (50 mM).

Figure 7:
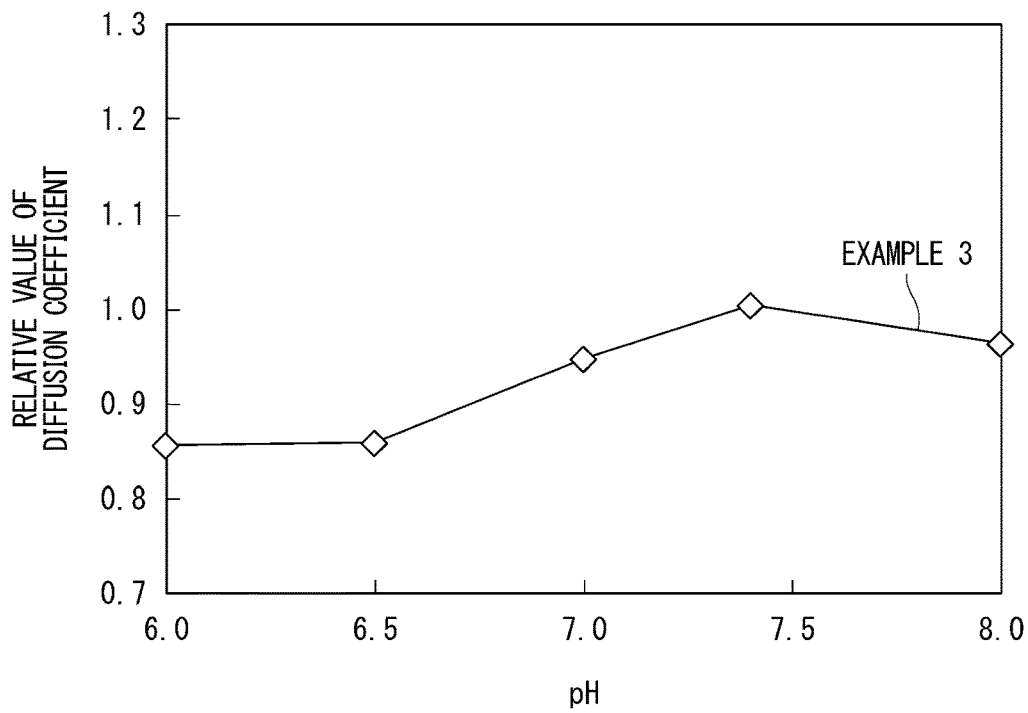
FIG. 7 is a graph showing results of measuring the diffusion coefficient of a polymer by fluorescence correlation spectroscopy in Experimental Example 8.

FIG. 7 is a graph showing measurement results by FCS. As a result, it was found that the polymer of Example 3 exhibited no interaction with heparin under conditions of pH corresponding to the peripheral environment of normal tissue (pH approximately 7.4), and formed aggregates with heparin (the diffusion coefficient decreased) under weakly acidic conditions (pH approximately 6.5) corresponding to the peripheral environment of a tumor.

These results showed that the polymer of Example 3 does not interact with cells of normal tissue, but specifically adsorbs to the cell membranes of the cells of tumor tissue and promotes incorporation into the cells.

Experimental Example 9

(Investigation of Incorporation of Polymer of Example 3 Into Cells)

The polymer of Example 3 was brought into contact with mouse colon cancer cells CT26 under various conditions of pH to investigate whether the polymer was incorporated into the cells or not. As described above, the polymer of Example 3 was PGlu (DET-Car) having an average degree of polymerization of 112.

First, 50,000 CT26 cells per well were seeded in 24-well plates and incubated overnight in a DMEM medium with 10% fetal bovine serum (FBS). Next, the medium was replaced with a pH 7.4 buffer (10 mM HEPES, 150 mM NaCl, 10% FBS) or a pH 6.5 buffer (10 mM phosphate buffer, 150 mM NaCl, 10% FBS).

Next, Cy3-labeled polymer was added to make a final concentration of 1 μM and incubated at 37° C. for 6 hours. Next, CT26 cells were subjected to a rinsing treatment with a buffer not including FBS, recovered by further performing a trypsinization treatment, and analyzed by flow cytometry (type "Guava easyCyte 6-2L", Merck Millipore), and the fluorescence intensity of Cy3 incorporated into the CT26 cells was measured.

Figure 8:
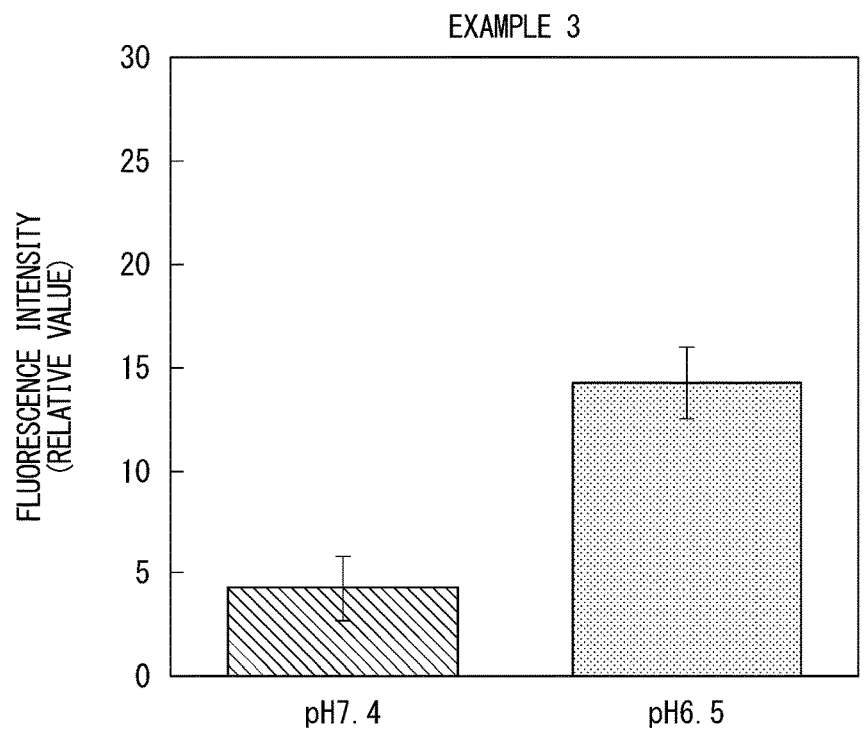
FIG. 8 is a graph showing the results of measuring polymer incorporation into cells by flow cytometry in Experimental Example 9.

FIG. 8 is a graph showing the results of flow cytometry. As a result, it was confirmed that the incorporation of the polymer of Example 3 into the cells at pH 6.5 increased as compared with pH 7.4.

Experimental Example 10

(Interaction Test of Polymer of Example 4 and Anionic Sugar Chain)

As described above in Experimental Example 1, in general, the surface of the cell membrane is covered with anionic sugar chains. Therefore, the pH-dependent interaction between the polymer of Example 4 and the anionic sugar chain was investigated. Heparin was used as the anionic sugar chain. As described above, the polymer of Example 4 was PGlu (DET-Sul) with an average degree of polymerization of 112.

First, PGlu (DET-Sul) was labeled with Cy3, which is a fluorescent substance. Next, a mixed solution of 200 nM of a polymer and 100 μg/mL of heparin was prepared and the diffusion coefficient of the polymer was measured using fluorescence correlation spectroscopy (FCS) under various conditions of pH (model "LSM 710" Carl-Zeiss). A decrease in the diffusion coefficient of the polymer indicates that heparin and the polymer interacted to form aggregates. Conditions of pH of pH 6.0, 6.5 and 7.0 were prepared with an MES buffer solution (50 mM) and conditions of pH of pH 7.4 and 8.0 were prepared with a HEPES buffer solution (50 mM).

Figure 9:
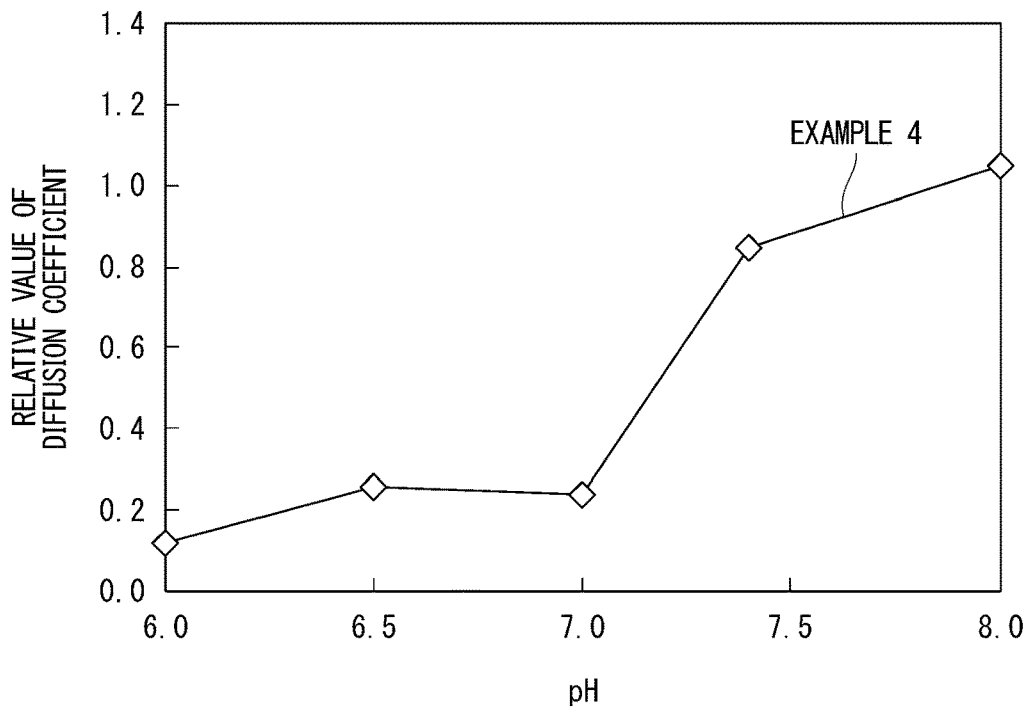
FIG. 9 is a graph showing results of measuring the diffusion coefficient of a polymer by fluorescence correlation spectroscopy in Experimental Example 10.

FIG. 9 is a graph showing measurement results by FCS. As a result, it was found that the polymer of Example 4 exhibited no interaction with heparin under conditions of pH (pH approximately 7.4) corresponding to the peripheral environment of the normal tissue, and aggregates with heparin were formed (the diffusion coefficient decreased) under weakly acidic conditions (pH approximately 6.5) corresponding to the peripheral environment of the tumor.

These results show that the polymer of Example 4 strongly interacts with the cell membrane of the cells of the tumor tissue as compared with the cells of the normal tissue, and the incorporation into the cells is promoted.

Experimental Example 11

(Investigation of Incorporation of Polymer of Example 4 Into Cells)

The polymer of Example 4 was brought into contact with mouse colon cancer cells CT26 under various conditions of pH to investigate whether the polymer was incorporated into the cells or not. As described above, the polymer of Example 4 was PGlu (DET-Sul) with an average degree of polymerization of 112.

First, 50,000 CT26 cells per well were seeded in 24-well plates and incubated overnight in DMEM medium with 10% fetal bovine serum (FBS). Next, the medium was replaced with a pH 7.4 buffer solution (10 mM HEPES, 150 mM NaCl, 10% FBS) or a pH 6.5 buffer solution (10 mM phosphate buffer solution, 150 mM NaCl, 10% FBS).

Next, a Cy3-labeled polymer was added to make a final concentration of 1 μM and incubated at 37° C. for 6 hours. Next, CT26 cells were subjected to a rinsing treatment with a buffer solution not including FBS, recovered by further performing a trypsinization treatment, and analyzed by flow cytometry (type "Guava easyCyte 6-2L", Merck Millipore), and the fluorescence intensity of Cy3 incorporated into the CT26 cells was measured.

Figure 10:
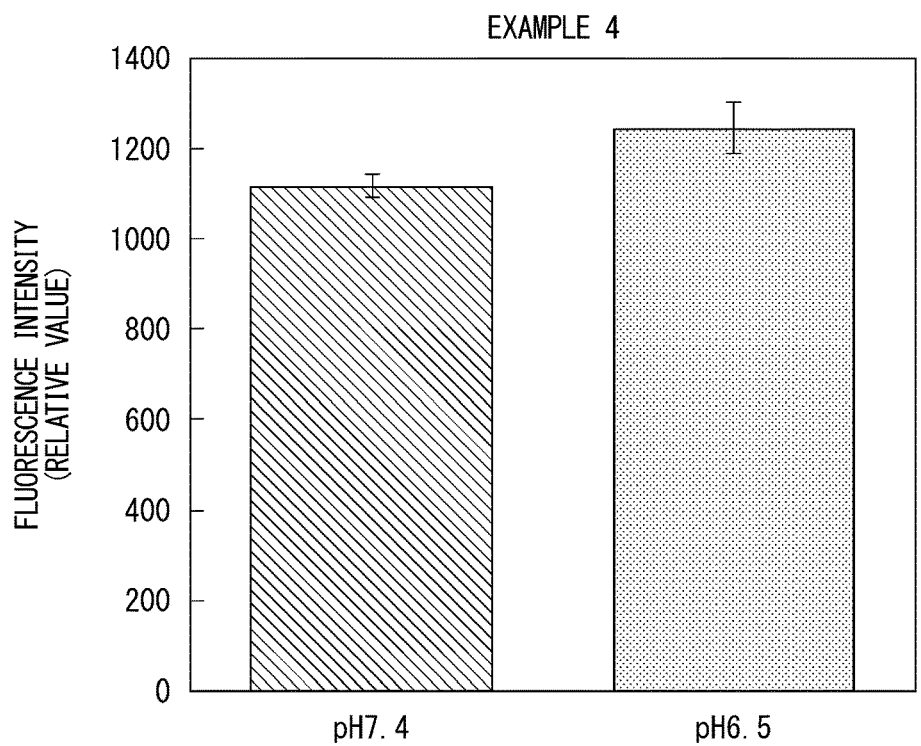
FIG. 10 is a graph showing results of measuring polymer incorporation into cells by flow cytometry in Experimental Example 11.

FIG. 10 is a graph showing the results of flow cytometry. As a result, it was confirmed that the incorporation of the polymer of Example 4 into the cells at pH 6.5 increased as compared with pH 7.4.

INDUSTRIAL APPLICABILITY

According to the present invention, it is possible to provide a polymer exhibiting a stealth property with respect to blood components and normal tissue, and with improved accumulation efficiency and incorporation efficiency into cells with respect to tumor tissue.

The invention claimed is:
1. A pH-responsive polymer, comprising:
a biocompatible polymer in which a side chain thereof including a group represented by Formula (1), a group represented by Formula (2), or a group represented by Formula (3) is bonded via a linking group containing an amide bond, wherein the biocompatible polymer is polyglutamic acid or polyaspartic acid, wherein the linking group containing an amide bond is bonded to the main chain of the biocompatible polymer, and the side chain is electrically neutral under pH environments of 7.2 to 7.6 and which changes to be cationic under pH environments of 6.0 to 6.6:

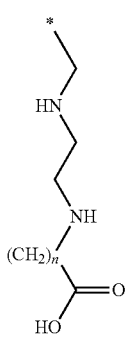

(1)

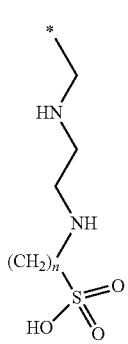

(2)

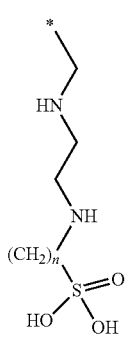

(3)

in Formulas (1) to (3), n represents an integer of 1 to 3, and * represents a bond.

2. The pH-responsive polymer according to claim 1, wherein the biocompatible polymer is biodegradable.

3. The pH-responsive polymer according to claim 1, comprising: a repeating unit represented by Formula (b).

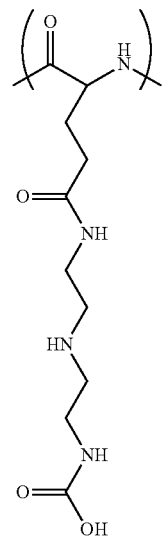

(b)

4. The pH-responsive polymer according to claim 1, comprising: a repeating unit represented by Formula (c)

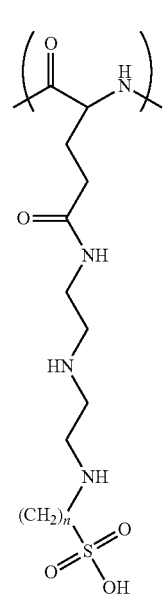

(c)

(in Formula (c), n represents 2 or 3).

5. The pH-responsive polymer according to claim 1, wherein a weight-average molecular weight is 1,000 to 200,000.

6. The pH-responsive polymer according to claim 5, wherein a weight-average molecular weight is 10,000 to 50,000.

7. The pH-responsive polymer according to claim 1, wherein 4 to 800 moles of the side chain which is electrically neutral under pH environments of 7.2 to 7.6 and which changes to be cationic under pH environments of 6.0 to 6.6 is bonded per one mole of the biocompatible polymer.

8. The pH-responsive polymer according to claim 1, which is for a drug delivery system.

9. A drug delivery system comprising, the pH-responsive polymer according to claim 1; and a drug bonded to the pH-responsive polymer.

\* \* \* \* \*